US010174334B2

(12) United States Patent
Reski et al.

(10) Patent No.: US 10,174,334 B2
(45) Date of Patent: Jan. 8, 2019

(54) MODIFIED EXPRESSION OF PROLYL-4-HYDROXYLASE IN PHYSCOMITRELLA PATENS

(71) Applicant: Baden Wuerttemberg Stiftung gGmbH, Stuttgart (DE)

(72) Inventors: Ralf Reski, Oberried (DE); Juliana Parsons, Breisach (DE); Friedrich Altmann, Vienna (AT); Manuela Graf, Hannover (DE); Eva Decker, Freiburg (DE); Johannes Stadlmann, Brunn/Gebirge (AT)

(73) Assignees: ALBERT-LUDWIGS-UNIVERSITAET FREIBURG, Freiburg (DE); UNIVERSITAET FUER BODENKULTUR WIEN, Vienna (AT)

(*) Notice: Subject to any disclaimer, the term of this patent is extended or adjusted under 35 U.S.C. 154(b) by 0 days.

(21) Appl. No.: 14/889,254

(22) PCT Filed: May 5, 2014

(86) PCT No.: PCT/EP2014/059132
§ 371 (c)(1),
(2) Date: Nov. 5, 2015

(87) PCT Pub. No.: WO2014/180793
PCT Pub. Date: Nov. 13, 2014

(65) Prior Publication Data
US 2016/0208275 A1 Jul. 21, 2016

(30) Foreign Application Priority Data
May 6, 2013 (GB) .................... 1308120.3

(51) Int. Cl.
C12N 15/82 (2006.01)
C12N 9/06 (2006.01)
C07K 14/505 (2006.01)
C12N 9/02 (2006.01)
C07K 14/415 (2006.01)
A61K 38/00 (2006.01)

(52) U.S. Cl.
CPC ........ *C12N 15/8242* (2013.01); *C07K 14/505* (2013.01); *C12N 9/0012* (2013.01); *C12N 9/0071* (2013.01); *C12N 15/8218* (2013.01); *C12N 15/8257* (2013.01); *A61K 38/00* (2013.01); *C07K 14/415* (2013.01); *C12Y 114/11002* (2013.01)

(58) Field of Classification Search
None
See application file for complete search history.

(56) References Cited

FOREIGN PATENT DOCUMENTS

| EP | 2360261 A1 | 8/2011 |
| JP | 2009-501011 | 1/2009 |
| KR | 10-2001-0105066 | 11/2001 |
| KR | 10-2007-0083870 | 8/2007 |
| WO | 0129242 A2 | 4/2001 |
| WO | 2007006570 A2 | 1/2007 |

OTHER PUBLICATIONS

Galbraith et al. Biosynthesis, processing and targeting of the G-protein of vesicular stomatitis virus in tobacco protoplasts. (1992) Planta; vol. 186; pp. 324-336.*
Vlad et al. *Arabidopsis* prolyl 4-hydroxylases are differentially expressed in response to hypoxia, anoxia and mechanical wounding. (2007) Physiologia Plantarum; vol. 130; pp. 471-483.*
Velasquez et al. O-glycosylated cell wall proteins are essential in root hair growth. (2011) Science; vol. 332; pp. 1401-1403.*
Oliver et al. Pythium infection activates conserved plant defense responses in mosses. (2009) Planta; vol. 230; pp. 569-579.*
Castilho et al. Engineering of sialylated mucin-type O-glycosylation in plants. (2012) Journal of Biological Chemistry; vol. 287; pp. 36518-36526.*
S. M. Velasquez et al: "0-Glycosylated Cell Wall Proteins Are Essential in Root Hair Growth," Science, vol. 332, No. 6036, Jun. 17, 2011 (Jun. 17, 2011), pp. 1401-1403.
Eva L. Decker et al: "Glycoprotein production in moss bioreactors," Plant Cell Reports, vol. 31, No. 3, Mar. 1, 2012 (Mar. 1, 2012 ), pp. 453-460.
Yoshikatsu Matsubayashi: "Recent progress in research on small post-translationally modified peptide signals in plants," Genes to Cells, vol. 17, No. 1, Jan. 23, 2012 (Jan. 23, 2012), pp. 1-10.
Juliana Parsons et al: "A gene responsible for prolylhydroxylation of moss-produced recombinant human erythropoietin," Re Item II: Scientific Reports, vol. 3, Oct. 22, 2013 (Oct. 22, 2013).
Yang, Z., et al., "Toward Stable Genetic Engineering of Human O-Glycosylation in Plants," Plant Physiology, Sep. 2012, vol. 160, pp. 450-463.
Silvia M. Velasquez et al., "O-Glycosylated Cell Wall Proteins Are Essential in Root Hair Growth," Science. vol. 332, No. 6036, pp. 1401-1403 (Jun. 17, 2011).
GenBank Accession No. XM_001753185 (May 22, 2009).
"*Physcomitrella patens* subsp. *patens* predicted protein" Gene Bank, NCBI Reference Sequence: XM_00175318_5.1, May 22, 2009 (download link: https://www.ncbi.nlm.nih.gov/nuccore XM_00175318S. 1).

*Primary Examiner* — Cathy Kingdon Worley
(74) *Attorney, Agent, or Firm* — 24IP Law Group; Timothy R DeWitt

(57) ABSTRACT

The field of the invention relates to a method for the production of a recombinant protein in a plant-based system comprising the steps of providing a plant-based system comprising a modulation for a plant endogenous prolyl-4-hydroxylase gene, delivering a gene encoding the recombinant protein into the plant-based system, and cultivating the plant-based system for the expression of the gene encoding the recombinant protein. The field of the invention further relates to a recombinant protein, which has been produced in a plant-based system. A plant-based system and use of the recombinant protein are also provided.

4 Claims, 13 Drawing Sheets

Specification includes a Sequence Listing.

(56) References Cited

OTHER PUBLICATIONS

"BioChancePLUS-3: Verbundprojekt: Entwicklung und Produktion neuartiger Biopharmazeutika im Moos," Veroffentlichung der Ergebnisse von Forschungsvorhaben im BMBF-Programm, 2011.

Y. Matsubayashi, "Recent progress in research on small post-translationally modified peptide signals in plants" Genes to Cells, 2012, vol. 17, No. 1, pp. 1-10.

E. Decker, R. Reski, "Glycoprotein production in moss bioreactors" Plant Cell Rep, 2012, vol. 31, No. 3, pp. 453-460.

Yang, et al., "Toward Stable Genetic Engineering of Human O-Glycosylation in Plants," Plant Physiology, 2012, vol. 160, pp. 450-463.

* cited by examiner

FIG. 1

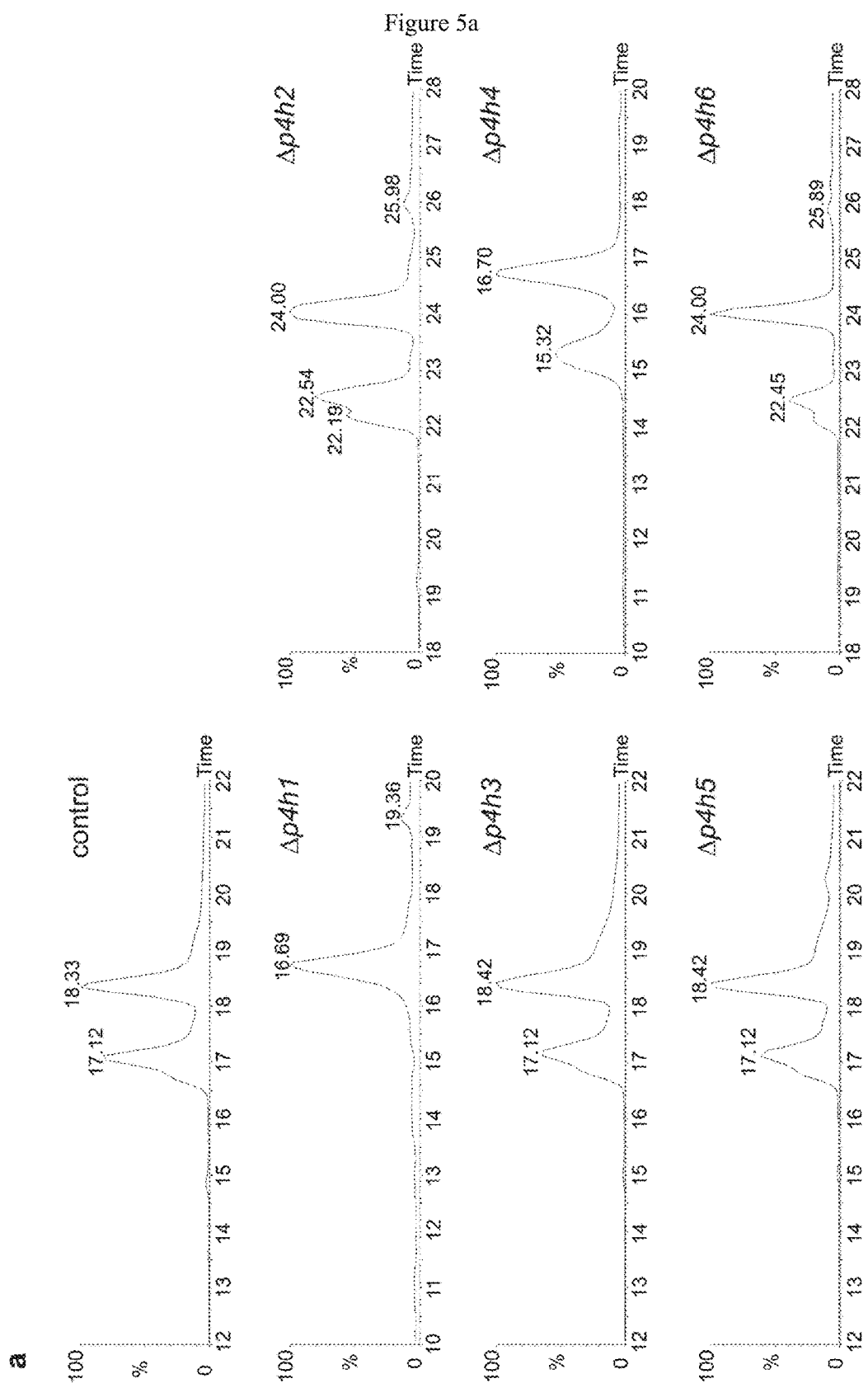

MODIFIED EXPRESSION OF PROLYL-4-HYDROXYLASE IN PHYSCOMITRELLA PATENS

The sequence listing electronically filed herewith is hereby incorporated by reference in its entirety (File Name: 2016-12-16_4091-80145_Seq_List.TXT; File Size: 49 KB; Date Created Dec. 16, 2016).

FIELD OF THE INVENTION

The present invention relates to a method for the production of a recombinant protein in a plant-based system, a recombinant protein, which has been produced in a plant-based system, a plant-based system and use of the recombinant protein.

BACKGROUND OF THE INVENTION

Recombinant production of pharmaceutical proteins is pivotal, not only for personalized medicine. While most biopharmaceuticals are produced in mammalian cell culture, plant-made pharmaceuticals (PMP) are gaining momentum with the first product released to the market (protalix.com). Although posttranslational modifications (PTMs) of plants are similar to those of humans, slight differences can affect quality, safety and efficacy of PMPs (Walsh and Jefferis, Nat. Biotechnol., 24:1241-1252, 2006). One of the most common PTMs in higher eukaryotes is prolyl-4-hydroxylase (P4H)-catalyzed prolyl-hydroxylation. P4H sequence recognition sites on target proteins differ between humans and plants leading to non-human PTMs. Moreover, in plants the resulting hydroxyprolines are the anchor for O-glycosylation which again differs from human O-glycosylation.

Plant-based systems are gaining acceptance as alternative production platforms for recombinant biopharmaceuticals (Paul and Ma, Biotechnol. Appl. Biochem., 58:58-67, 2011). With regard to slight differences in post-translational modifications between humans and plants considerable progress was achieved in the humanization of Asparagin (N)-linked glycosylation of PMPs (Karnoup et al., Glycobiology, 15:965-981, 2005; Pinkhasov et al., Plant Biotechnol. J., 9:991-1001, 2011; Weise et al., Plant Biotechnol. J., 5:389-401, 2007; Cox et al., Nat. Biotechnol., 24:1591-1597, 2006). The attachment of immunogenic plant-specific β1,2-xylose and α1,3-fucose residues to the core N-glycan was abolished in different plant systems (Cox et al., Nat. Biotechnol., 24:1591-1597, 2006; Koprivova et al., Plant Biotechnol. J., 2:517-523, 2004; Strasser et al., FEBS Lett., 561:132-136, 2004; Sourrouille et al., Plant Biotechnol. J., 6:702-721, 2008). In addition, the elimination of Lewis A epitopes on N-glycans of rhEPO was reported recently (Parsons et al., Plant Biotechnol. J., 10:851-861, 2012). Further humanization of the N-glycosylation on PMPs was achieved by expression of the human β1,4 galactosyltransferase (Bakker et al., Proc. Natl. Acad. Sci. U.S.A, 103:7577-7582, 2006; Huether et al., Plant Biol. (Stuttg.), 7:292-299, 2005) and additional heterologous enzymes necessary for engineering sialylation (Castilho et al., J. Biol. Chem., 285:15923-15930, 2010). Despite this progress in humanizing N-glycosylation, differences in O-glycosylation can affect product quality. Plant O-glycosylation differs explicitly from the typical human mucin-type O-glycosylation (Gomord et al., Plant Biotechnol. J., 8:564-587, 2010) and induces antibody formation in mammals (Leonard et al., J. Biol. Chem., 280:7932-7940, 2005; Yates et al., Glycobiology, 6:131-139, 1996). Immunogenicity of biopharmaceuticals may result in reduced product efficacy and is a potential risk for the patients (Schellekens, Nat. Rev. Drug Discov., 1:457-462, 2002). Such adverse effects hamper the broad use of plants as production hosts for biopharmaceuticals. In plants, the main anchor for O-glycosylation is 4-trans-hydroxyproline (Hyp) (Kieliszewski, Phytochemistry, 57:319-323, 2001), while no further modification of Hyp occurs in mammals (Gorres and Raines, Crit. Rev. Biochem. Mol. Biol., 45:106-124, 2010). Although Hyp is always synthesized posttranslationally by prolyl-4-hydroxylases (P4Hs) via hydroxylation of the γ carbon of proline, recognition sites differ between mammals and plants (Gorres and Raines, Crit. Rev. Biochem. Mol. Biol., 45:106-124, 2010). Hyp is an important structural component of plant cell walls and of the extracellular matrix of animals and humans. Here, Hyp plays a key role in stabilizing the structure of collagen, one of the most abundant proteins in mammals, where the second proline of the tripeptide PPG is usually hydroxylated by collagen P4Hs. In plants, Hyp residues are the attachment sites for O-glycosylation in hydroxyproline-rich glycoproteins (HRGPs), the most abundant proteins in the plant extracellular matrix and cell wall. HRGPs include extensins, proline-rich glycoproteins and arabinogalactan proteins (AGPs) (Kieliszewski, Phytochemistry, 57:319-323, 2001; Kieliszewski and Lamport, Plant J., 5:157-172, 1994; Shpak et al., J. Biol. Chem., 276:11272-11278, 2001). Prolyl-hydroxylation and subsequent glycosylation of plant cell wall proteins is of major importance for growth, differentiation, development and stress adaption (Velasquez et al., Science, 332:1401-1403, 2011; Lamport et al., New Phytol., 169:479-492, 2006).

The target motifs for Hyp-anchored O-glycosylation in plants, so-called glycomodules, were defined and validated (Kieliszewski and Lamport, Plant J., 5:157-172, 1994; Shpak et al., J. Biol. Chem., 276:11272-11278, 2001). From these, the consensus motif $[A/S/T/V]-P_{(1,4)}-X_{(0,10)}-[A/S/T/V]-P_{(1,4)}$ (where X can be any amino acid) was derived for predicting prolyl-hydroxylation in plants (Gomord et al., Plant Biotechnol. J., 8:564-587, 2010). According to in silico analysis of the human proteome, approximately 30% of all proteins contain this motif, and are thus candidates for non-human prolyl-hydroxylation and subsequent O-glycosylation when expressed in plants (Gomord et al., Plant Biotechnol. J., 8:564-587, 2010). Consequently, adverse plant-typical prolyl-hydroxylation and even arabinosylation of PMPs was reported (Karnoup et al., Glycobiology, 15:965-981, 2005; Pinkhasov et al., Plant Biotechnol. J., 9:991-1001, 2011; Weise et al., Plant Biotechnol. J., 5:389-401, 2007). On the other hand, the artificial introduction of Hyp-O-glycosylation in PMPs was suggested as an alternative to PEGylation to increase the serum half-life of biopharmaceuticals (Xu et al., Biotechnol. Bioeng., 97:997-1008, 2007; US patent application 20060026719). However, non-human prolyl-hydroxylation does not only alter the native sequence of the protein, but also serves as anchor for O-glycans, which in turn may be immunogenic. Thus, the elimination of the anchor Hyp is the only safe way to avoid adverse O-glycosylation in PMPs.

The three documents EP 2 360 261 A1, Xu et al. (BMC Biotechnol, 11:69, 2011) and Stein et al. (Biomacromolecules, 10:2640-2645) each deal with the production of collagen in different plant systems (e. g. maize, tobacco). Mammalian- or human-specific prolyl hydroxylation is achieved by expression of exogenous mammalian/human prolyl 4 hydroxylase. Thus, the disclosed methods in all three documents require expression of exogenous mammalian/human prolyl 4 hydroxylase.

Among plants, the moss *Physcomitrella patens* offers the unique possibility for precise and targeted genetic engineering via homologous recombination (e.g. Strepp et al., Proc. Natl. Acad. Sci. U.S.A, 95:4368-4373, 1998; Koprivova et al., Plant Biotechnol. J., 2:517-523, 2004). Further, several PMPs have been produced in the moss bioreactor, including rhEPO (Decker and Reski, Plant Cell Rep., 31:453-460, 2012), the leading biopharmaceutical world-wide. Its market turnover is over 10 billion Euros per year. EPO is a highly glycosylated peptide hormone stimulating erythropoiesis. Recombinant hEPO produced in CHO (Chinese hamster ovary) cells is used for prevention or treatment of anemia in nephrology and oncology patients, and can be abused for illegal doping activities. A glyco-engineered version of EPO (asialo-EPO) has no hematopoietic activity but can serve as a safe drug with neuro- and tissue-protective functions after stroke and additional hypoxia stress (Erbayraktar et al., Proc. Natl. Acad. Sci. U.S.A, 100:6741-6746, 2003). Production of correctly N-glycosylated asialo-EPO in the moss bioreactor was reported recently (Parsons et al., Plant Biotechnol. J., 10:851-861, 2012). However, plant-derived rhEPO is hydroxylated within the motif SPP (147-149) (Weise et al., Plant Biotechnol. J., 5:389-401, 2007) and thus may have adverse effects on patients.

Weise et al. (Plant Biotechnol. J., 5:389-401, 2007) and Parsons et al. (Plant Biotechnol. J., 10:851-861, 2012) both deal with the production of rhEPO in moss and with the modulation of the glycosylation pattern of N-glycans by targeting the plant-specific fucosyl-/xylosyl-/galactosyl-transferases. Thereby, immunogenic fucoses/xyloses/galactoses on the N-glycans are removed. Both documents do not address O-glycosylation because prolyl hydroxylation (as an anchor for O-glycosylation) is not subject of these disclosures.

The hydroxylation of prolines of a recombinant human protein produced in a plant-based system cannot be obviated so far. It only becomes apparent after production of a recombinant human protein if its prolines are hydroxylated and if non-human or plant specific O-glycosylation is present.

It is an object of the present disclosure to provide a method for the production of a recombinant protein using a plant-based system. It is also an object of the present disclosure to provide a recombinant protein, which has been produced in a plant-based system without the need to introduce exogenous prolyl-4-hydroxylase genes into the system, wherein the recombinant protein does not comprise any non-human prolyl hydroxylation. It is further an object of the present disclosure to provide a plant-based system used for the production of such a recombinant protein and to provide a use of such a recombinant protein.

BRIEF DESCRIPTION OF THE INVENTION

The present disclosure provides a method for the production of a recombinant protein comprising no or only human-specific prolyl hydroxylation in a plant-based system. The method comprises the steps of providing a plant-based system comprising a modulation for a plant endogenous prolyl-4-hydroxylase gene, delivering a gene encoding the recombinant protein into the plant-based system and cultivating the plant-based system for the expression of the gene encoding the recombinant protein. It is obvious for a person ordinary skilled in the art that purification of the protein will be a prerequisite for using the recombinant protein for any further processing like the production of a pharmaceutical.

In this method, the plant-based system may comprise plant cells derived from *Physcomitrella patens*. The prolyl-4-hydroxylase gene may be the *Physcomitrella patens* prolyl-4-hydroxylase gene with the NCBI Accession No. XM_001753185. The recombinant protein may be recombinant human erythropoietin (rhEPO).

The present disclosure also provides a recombinant protein that has been produced in a plant-based system comprising a modulation for a plant endogenous prolyl-4-hydroxylase gene. The recombinant protein is produced by above-described method. It is intended that the recombinant protein does not comprise any non-human prolyl hydroxylation. It is also within the scope of the present disclosure if such a protein does not comprise plant specific prolyl hydroxylation, which means that plant specific prolyl hydroxylation may not be present at at least one plant-specific prolyl hydroxylation site in order to avoid any immunological or side effects in the species of origin of the recombinant protein.

Regulation of gene expression includes a wide range of mechanisms that are used by cells to up-regulate or down-regulate the production of specific gene products (proteins or RNA). The regulation of transcription affects mRNA production, while the regulation of translation affects protein production. Even post-translational modifications may affect the regulation of successful gene expression. A person skilled in the art has relevant knowledge about technologies suitable for up- or down-regulation of gene or protein expression. Thus, the term "down-regulation of gene expression" designates a decrease in gene or protein expression compared to the unmodified state.

Modulation or modification of a gene, gene activity or gene expression according to the present disclosure refers to activation or up-regulation as well as to down-regulation or a knock-out of a gene, gene activity or gene expression. Complete ablation of gene expression can be achieved by a knock-out of the gene, but also by mutations with nuclease technologies (TALEN, CRISPR-Cas) or by the identification of plant mutants from collections which have undergone x-ray treatment, EMS-mutagenesis or T-DNA insertion. Down-regulation can be achieved by amiRNA or other conventional techniques. Techniques for up-regulation, down-regulation or knock-out of a gene are comparable in all plants.

The plant-based system may comprise plant cells derived from *Physcomitrella patens*. The modulated prolyl-4-hydroxylase gene may be the *Physcomitrella patens* prolyl-4-hydroxylase gene with the NCBI Accession No. XM_001753185.

In a further embodiment of the present disclosure, the recombinant protein is recombinant human erythropoietin (rhEPO).

The present disclosure also provides a plant-based system comprising a modulation of a plant endogenous prolyl-4-hydroxylase gene. The plant-based system may comprise plant cells derived from *Physcomitrella patens* and the prolyl-4-hydroxylase gene can be the *Physcomitrella patens* prolyl-4-hydroxylase gene with the NCBI Accession No. XM_001753185. Such a system may be used for the production of a recombinant protein, wherein the recombinant protein only comprises human-specific prolyl hydroxylation or lacks prolyl hydroxylation at at least one plant specific prolyl hydroxylation site.

The plant-based system may be the *Physcomitrella patens* mutant deposited with the International Moss Stock Center under IMSC No. 40218.

A use of a modulated prolyl-4-hydroxylase gene of *Physcomitrella patens* for the manufacture of recombinant proteins is a further object of the present disclosure.

It is a further object of the present disclosure to use the recombinant protein as a pharmaceutical or biopharmaceutical. It is obvious for a person ordinary skilled in the art, that it is also within the scope of the present disclosure that the recombinant protein may be part of a pharmaceutical in combination with other compounds.

BRIEF DESCRIPTION OF THE FIGURES

Figure 1:
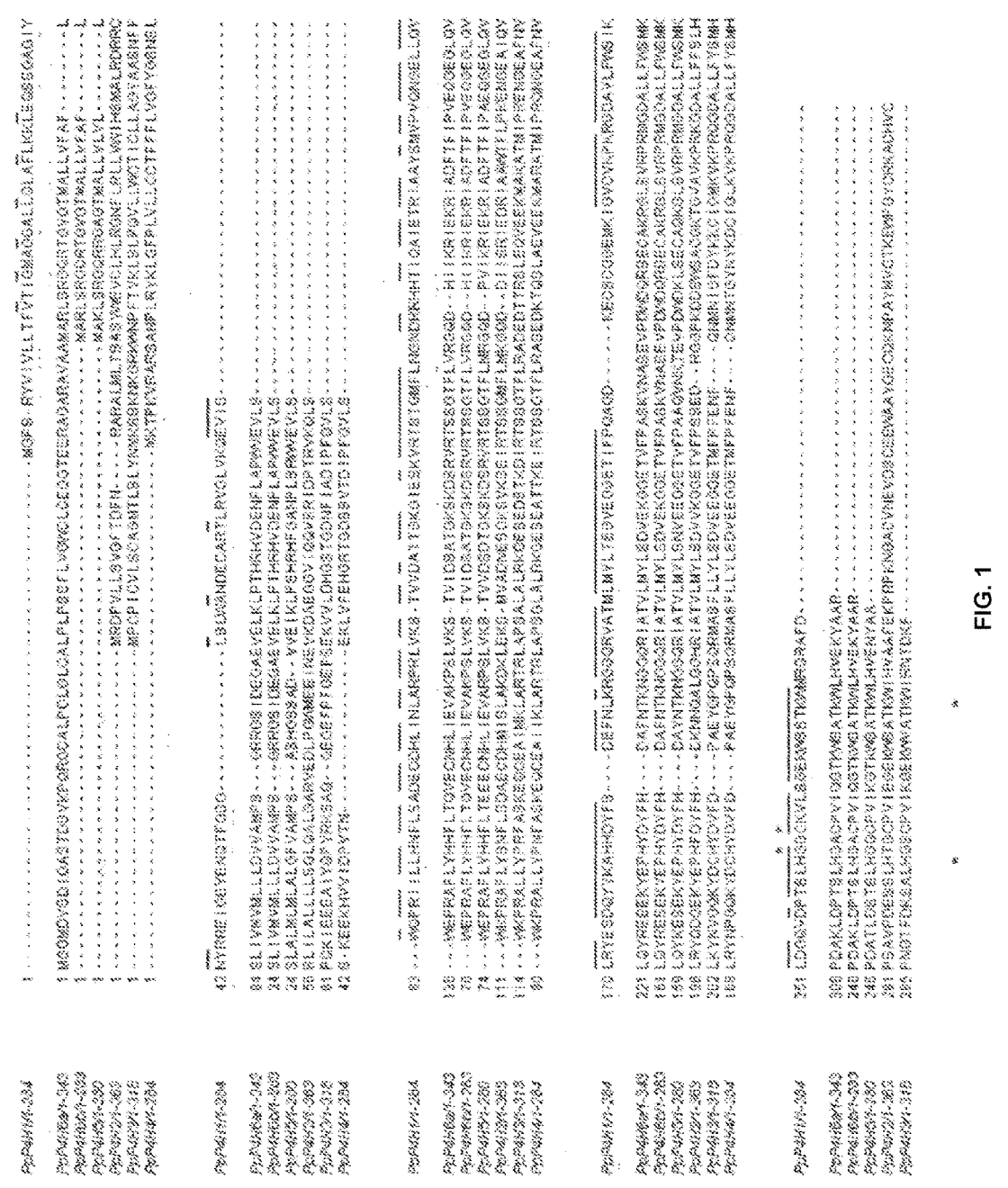

FIG. 1 Protein sequence comparison of *P. patens* putative prolyl-4-hydroxylases (P4Hs): PpP4H1 (SEQ ID No: 2), PpP4H6a (SEQ ID No: 12), PpP4H6b (SEQ ID No: 14), PpP4H5 (SEQ ID No: 10), PpP4H2 (SEQ ID No: 4), PpP4H3 (SEQ ID No: 6), PpP4H4 (SEQ ID No: 8).

DETAILED DESCRIPTION OF THE INVENTION

Figure 2:
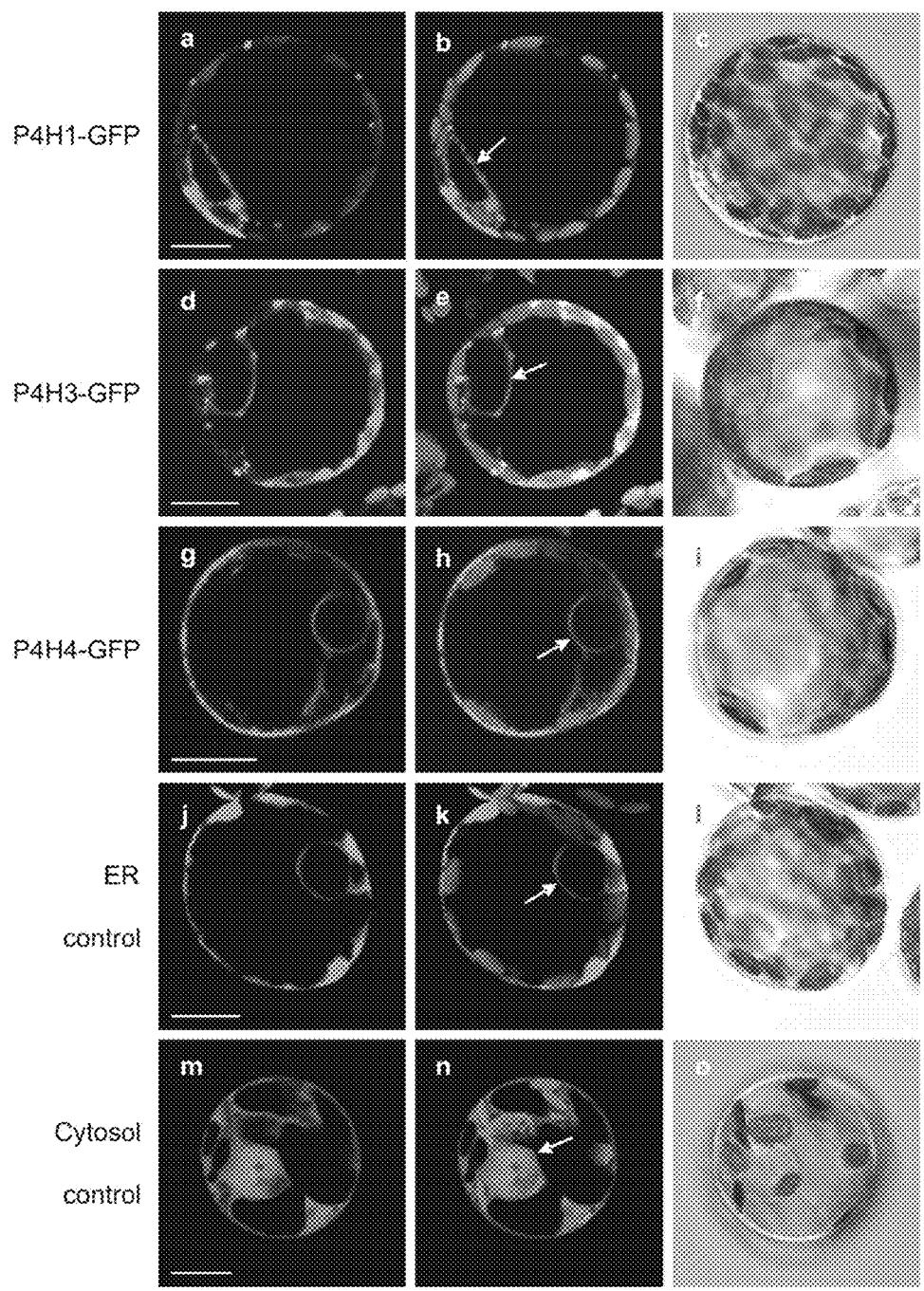
FIG. 2 In vivo subcellular localization of *P. patens* P4H homologues

The present disclosure provides a method for the production of a recombinant protein comprising only human-specific prolyl hydroxylation in a plant-based system, comprising the steps of providing a plant-based system, wherein the plant-based system comprises a modulation for a plant endogenous prolyl-4-hydroxylase gene, delivering a gene encoding the recombinant protein into the plant-based system, and cultivating the plant-based system for the expression of the gene encoding the recombinant protein.

The term "plant endogenous" shall refer to the plant's own prolyl hydroxylase gene. In other words, if the plant-based system comprises plant cells derived from *Physcomitrella patens*, the prolyl-4-hydroxylase gene is also derived from *Physcomitrella patens*. It is not intended to insert an additional mammalian gene.

The delivery of DNA shall be understood as the introduction of DNA into cells and tissue. Any known method in the state of the art may be used, for example transformation, particle bombardment, electroporation or viral transduction.

Cultivation shall mean any type of cultivating technique known in the art using amongst standard laboratory equipment the appropriate media and substituents and cultivation conditions for the respective cells.

It was unexpectedly shown that the method reveals recombinant proteins, which may comprise only human-specific prolyl hydroxylation meaning that all plant-specific prolyl hydroxylations can be eliminated.

In this method, the plant-based system may comprise plant cells derived from *Physcomitrella patens*. The prolyl-4-hydroxylase gene may be the *Physcomitrella patens* prolyl-4-hydroxylase gene with the NCBI Accession No. XM_001753185. The recombinant protein may be recombinant human erythropoietin (rhEPO).

The present disclosure also provides a recombinant protein, which has been produced in a plant-based system according to above-described method. The plant-based system therefore comprises modulation of a plant endogenous prolyl-4-hydroxylase gene. The recombinant protein may only comprise human-specific prolyl hydroxylation or shall not have plant-specific prolyl hydroxylation at at least one plant specific prolyl hydroxylation site.

A plant-based system refers to plant cells or cells derived from plant cells. A plant-based system comprising a knockout allele shall mean that the plant-based system is genetically modified so that a wild-type allele of the gene is replaced by an engineered construct. The expression of the respective gene can thus be down-regulated or completely abolished. It has to be noted that even the down-regulation of a single p4h gene has been shown to be sufficient.

The plant-based system before genetic modification can be wildtype or mutant. "Wildtype" sequences within the meaning of the present disclosure refer to the non-mutated version of a gene common in nature or the allele required to produce the wildtype phenotype. The wildtype phenotype is the most common form or phenotype in nature or in a natural breeding population.

Recombinant proteins are derived from DNA sequences that in turn result from the use of molecular cloning to bring together genetic material from multiple sources, creating sequences that would not otherwise be found in biological organisms. A recombinant human protein for instance is derived from human DNA sequences which have been modified by genetic material from multiple sources.

Human-specific prolyl hydroxylation shall mean that the recombinant human protein comprises no plant-specific prolyl hydroxylations. Plant-specific prolyl hydroxylation is the hydroxylation of prolines, which is performed by the plant's unmodulated enzymes. Thus, when a recombinant human protein is expressed in a plant-based system, the plant's enzymes will hydroxylate the prolines in a plant-specific manner, giving rise to non-human O-glycosylation of the recombinant human protein. Thus, elimination of the plant-specific prolyl hydroxylation has the advantage that adverse O-glycosylation is avoided. Recombinant human proteins produced in a plant-based system can thus be humanized via glyco-engineering.

Given the great importance of O-glycosylated proteins for the human body, even slight differences between recombinant human proteins produced in a plant-based system and their native human counterparts in this posttranslational modification will hamper approval of the drug by the relevant authorities. Thus, the present approach is to precisely eliminate the attachment sites for plant-specific O-glycosylation, hydroxylated proline residues, on the recombinant human protein.

The plant-based system may comprise plant cells derived from *Physcomitrella patens*. The prolyl-4-hydroxylase gene may be the *Physcomitrella patens* prolyl-4-hydroxylase gene with the NCBI Accession No. XM_001753185.

It was unexpectedly shown that ablation of the gene with the NCBI Accession No. XM_001753185 can abolish undesired prolyl hydroxylation. Surprisingly, growth rate, differentiation, rhEPO productivity and secretion of the protein to the culture medium were not impaired in these knockout plants compared to the parental line.

*Physcomitrella patens* shall refer to the wildtype or the mutated moss.

In a further embodiment of the present disclosure, the recombinant protein is recombinant human erythropoietin (rhEPO).

The present disclosure also provides a plant-based system comprising a modulation for a plant endogenous prolyl-4-hydroxylase gene, wherein the plant-based system comprises plant cells derived from *Physcomitrella patens* and wherein further the prolyl-4-hydroxylase gene is the *Physcomitrella patens* prolyl-4-hydroxylase gene with the NCBI Accession No. XM_001753185 for the production of a recombinant protein, wherein the recombinant protein does not comprise any non-human prolyl hydroxylation.

The plant-based system may be the *Physcomitrella patens* mutant deposited with the International Moss Stock Center under IMSC No. 40218.

It is a further object of the present disclosure to use the recombinant protein as a pharmaceutical, including biopharmaceuticals, or for the manufacture of a pharmaceutical.

Biopharmaceuticals are pharmaceuticals produced using biotechnological means. They can be, for example, proteins (including antibodies) or nucleic acids (DNA, RNA or antisense oligonucleotides) and can be used for therapeutic or in vivo diagnostic purposes. They are produced by means other than direct extraction from a native (non-engineered) biological source. For example, biopharmaceuticals can be produced in genetically modified plants.

It is intended that the recombinant protein of the present disclosure can be used as a biopharmaceutical because it does not comprise non-human prolyl hydroxylation and no plant-specific prolyl hydroxylation.

EXPERIMENTS

Experiment 1: Identification of *Physcomitrella patens* prolyl-4-hydroxylases (P4Hs)

For the identification of prolyl-4-hydroxylase homologues in *P. patens*, the amino acid sequence of the *Arabidopsis thaliana* P4H1 (AT2G43080.1) was used to perform a BLAST (basic local alignment search tool) search against the gene models in the *Physcomitrella patens* resource (cosmoss.org). Six sequences from the *Physcomitrella patens* genome with homology to P4H enzymes were identified: Pp1s8_114V6.1 (PpP4H1), Pp1s192_51V6.1 (PpP4H2), Pp1s19_322V6.1 (PpP4H3), Pp1s172_91V6.1 (PpP4H4), Pp1s12_247V6.1 (PpP4H5) and Pp1s328_29V6.1 (PpP4H6). As sequence information was not complete for Ppp4h2, 3 and 6 mRNA, 5' RACE (rapid amplification of cDNA-ends)-PCR was employed (GeneRacer™, Invitrogen, Karlsruhe, Germany) according to the manufacturer's protocol to obtain full length sequences. Two different cDNAs were amplified for the Ppp4h6 gene, corresponding to alternative splice forms of the mRNA, from which two protein variants with different N-termini could be predicted (Ppp4h6a and Ppp4h6b).

The following sequences were identified:

P4H1cDNA (Pp1s8_114V6.1 Accession No.:
XM_001753185; SEQ ID NO. 1)
GCAAGATCGTCTGATTGCGCGCACGTCGGAGATCGCTTAAAGTGAAGGTT

GCATTGCTCTGGCAAGAAGTATTTGCAGGTAGGACGGTAGAGTCTGGATG

CGCCAGAGTTGTCGGTTTGGCCTTCTTCGCAAGGGAGAAGAAGTCATGAT

GCTTGGATTTAGCGAATTCGAAGAGCTGATCCTTGTTTTTCCGTCAGACT

-continued
GGCAAGGGATGGAGTAATTCTACGAAGCGAGCGCGTCAGGGTTTGGTTTT

AGGAAGCTGGGCTGCCACAGACACTTTTGACGATGGGTCCCTCTAGATAT

GTCATTGTGCTCCTCACATTTGTGACGATCGGCATGGCTGGGGGGGCGTT

ATTGCAGCTGGCTTTCTTGAAGAAGCTAGAACAAAGTAGTGGAGCTGGGA

TTTACAATTATAGAAGAGAGATAGGGGAATACGAAAACCAAACATTTGGA

TCGGGATTGTCCCTTTGGGCTAATGATGAAGATGCGAGAACACTACGTGT

TGGACTGGTTAAGCAAGAAGTTATTAGCTGGCAACCCAGAATCATTCTCC

TGCACAATTTCCTTAGTGCTGATGAATGTGATCACCTGATAAATCTTGCT

CGCCCCAGGCTCGTGAAGTCAACAGTCGTGGATGCAACCACAGGCAAGGG

AATCGAGAGTAAGGTTCGAACAAGCACAGGCATGTTCCTTAATGGAAATG

ACCGCAGACATCACACTATTCAGGCAATCGAAACCCGTATTGCTGCGTAT

TCTATGGTACCTGTTCAAAATGGGGAGCTCCTCCAAGTTTTACGATATGA

ATCTGATCAATATTACAAGGCACATCACGACTACTTTTCAGATGAGTTCA

ATTTAAAAAGGGGTGGGCAACGTGTGGCGACAATGCTTATGTACTTGACC

GAGGGGGTCGAGGGAGGCGAAACAATATTTCCGCAGGCTGGAGATAAAGA

GTGTAGCTGTGGCGGTGAAATGAAAATCGGCGTCTGTGTGAAACCTAAAC

GAGGGGATGCTGTCCTGTTTTGGAGCATTAAGCTGGATGGACAAGTTGAT

CCAACAAGCCTTCATGGTGGATGCAAAGTTTTGTCAGGAGAGAAATGGTC

GTCTACCAAATGGATGAGGCAGCGAGCCTTTGATTAGGGTGAACTTTGGA

TGGTAGGAGCTGTAATCATAGTAGAAGACCAATAATAGCGATTATGCCTC

ATCATTCCGGAAGCTTTGCGGGCTTTTCCCGATGCATCTAAGAATGTATG

TAATGAGCAACTTTGAATACTGTCAGTGATTCGTAACAAGAAAAAAATCG

ATTTAGTGGTATTGTGGACTTTGAAATGAAGGTTAAGATCACGAAGAGCT

TT

Translation corresponding to P4H1cDNA
(SEQ ID NO. 2)
MGPSRYVIVLLTFVTIGMAGGALLQLAFLKKLEQSSGAGIYNYRREIGEY

ENQTFGSGLSLWANDEDARTLRVGLVKQEVISWQPRIILLHNFLSADECD

HLINLARPRLVKSTVVDATTGKGIESKVRTSTGMFLNGNDRRHHTIQAIE

TRIAAYSMVPVQNGELLQVLRYESDQYYKAHHDYFSDEFNLKRGGQRVAT

MLMYLTEGVEGGETIFPQAGDKECSCGGEMKIGVCVKPKRGDAVLFWSIK

LDGQVDPTSLHGGCKVLSGEKWSSTKWMRQRAFD

P4H2cDNA (Pp1s192_51V6.1 Accession No.: JX964780;
SEQ ID NO. 3)
GTGATGCGTGATCCTGTGCTGCTGAGCGTGGGTTTTACCGACTTTAATCG

GGCAAGGGCGTTGATGTTAACTTCTGCATCGTACTGGGAGGTTTGTCTAC

ATCTCCGCGGGAATTTTCTGCGTCTTTTGGTGTGGATCCACAGCATGGCG

TTGAGAGATAGAAGATGTAGTCTTATTCTAGCTCTCTTATTACTATCGGG

ATTACAAGCATTGGGAGCTCGTGTGGAAGACTTGCCTGGTTGGATGGAAG

AAATCAATGAGGTGAAGGATGCTGAGGGTGGCGTGATTCAACAAGTTTCT

AGGATTGATCCCACTCGTGTCAAGCAGCTTTCGTGGAAACCGCGTGCATT

TCTATATTCAAACTTTTTGTCAGATGCAGAGTGTGATCATATGATATCGT

TGGCAAAGGACAAGCTGGAGAAGTCAATGGTGGCCGATAATGAATCTGGG

-continued
AAGAGTGTGAAGAGTGAAATTCGCACTAGCTCAGGTATGTTTTTGATGAA
GGGTCAGGATGATATCATATCAAGGATTGAGGATAGGATTGCTGCATGGA
CCTTTCTACCGAAGGAGAATGGGGAGGCAATCCAGGTCTTGAGGTACCAA
GATGGGGAGAAGTATGAGCCACATTTTGATTATTTCCACGATAAGAACAA
TCAGGCTCTTGGAGGTCACCGCATTGCCACTGTGTTAATGTACCTCTCCG
ACGTCGTCAAAGGTGGAGAGACAGTATTTCCTTCTTCTGAAGATCGAGGT
GGTCCCAAGGATGATTCGTGGTCTGCTTGTGGGAAAACTGGGGTGGCCGT
GAAACCAAGGAAAGGCGATGCCCTGCTCTTCTTCAGCCTACACCCCTCTG
CAGTTCCAGATGAGTCAAGCTTACACACAGGATGCCCAGTTATCGAAGGG
GAGAAATGGTCTGCTACAAAGTGGATCCATGTTGCTGCATTTGAAAAGCC
GCGTCCTAAGAATGGTGCATGTGTAAATGAGGTCGACAGTTGCGAAGAGT
GGGCAGCTTATGGGGAATGTCAGAAAAATCCAGCCTACATGGTTGGGACA
AAAGAGTGGCCAGGCTATTGCCGGAAAGCATGCCATGTGTGCTAGGTAGG
GATATACCGTATTTCTTGGTTGCACTCTGTTGGGTTAGGGTAGGATATTT
AATGTATTTGTGTCATCATCTAAGTATTAGGTCAGTTTCCAAACCAAGGA
ATCAGAGTTGTGGCTTTTGAAGAAGTATTATAGATCTTACGTACTAATTA
AAAGGCTTGTGACCCTTGAGATGCACTTTATAAT Translation corresponding to P4H2cDNA
(SEQ ID NO. 4)
MRDPVLLSVGFTDFNRARALMLTSASYWEVCLHLRGNFLRLLVWIHSMAL
RDRRCSLILALLLLSGLQALGARVEDLPGWMEEINEVKDAEGGVIQQVSR
IDPTRVKQLSWKPRAFLYSNFLSDAECDHMISLAKDKLEKSMVADNESGK
SVKSEIRTSSGMFLMKGQDDIISRIEDRIAAWTFLPKENGEAIQVLRYQD
GEKYEPHFDYFHDKNNQALGGHRIATVLMYLSDVVKGGETVFPSSEDRGG
PKDDSWSACGKTGVAVKPRKGDALLFFSLHPSAVPDESSLHTGCPVIEGE
KWSATKWIHVAAFEKPRPKNGACVNEVDSCEEWAAYGECQKNPAYMVGTK
EWPGYCRKACHVC P4H3cDNA (Pp1s19_322V6.1 Accession No.:
JX964781; SEQ ID NO. 5)
CGGCGCTTTGCAACTCCAATTTTGACCAGGCGAAGTGCACTTTGACATCT
TGTTGAATGTCCTCTTCTAGAGCATTGAACGGCCCTTCTGTGAACATTTT
AAACTATTCAACGGATGCCATTGACAGTCGTGGTTTTTGAAGTTCGAATC
CAGAGCCCTCGCCATCAAATCGTTGCAGTAATCCTTGGTGATTTAGCAAG
CTCGGGATCACTTCATGGATTTGGGGTCCTTCCTCTGCAGAGGCTGTTAG
TACACACACACTGCATCAACTCCTACTGGTCTGGAAGCTTTTGAGGTTGG
AAATAGTATGAAAGAGTCCCAGACAATTGGTGTATTGAGTGGAAGAGGGT
TGTGAAGTTTGGGCGCTCGACTGAAATGACCTGCGTGGATGTTAGAAAAT
AAGCCAATTGGTGTTATGTAGAGATTCGTCACAACGCCCTCATTCCTCCA
ACCCTTAAATGCCTTGCCCTATTTGTGTACTCTCGTGTGCGGGAATGACG
CTGTCCTTATACAATATGAAGTCATCGAAAAACAAAGGAAGAAAATGGAA
TCCTTTTACATACAAGCTCAGTTTGCCACAGGTGCTATTGTGGTGCACAA
TCTGCCTCTTAGCAGGCTATGCCGCCTCCAATTTCTTCCCCCAGAAAATA GAAGAGGAAGCAATATATCAGCCGTATCGGAAATCGGCTCAGCAAGAAGG
GGAATTTCCATTTGGTGAATTCAGTGAAAAAGTGGTGTTAGATCATGGTA
GCACTGGGGACAACTTCATCGCTGACATTCCTTTCCAGGTGTTGAGCTGG
AAGCCTCGTGCGCTCTTGTATCCGAGATTTGCTAGCAAGGAGCAATGCGA
GGCCATCATGAAGCTTGCAAGGACTCGTCTTGCTCCTTCTGCTCTGGCTT
TGAGGAAAGGGGAGAGTGAAGACTCAACGAAAGACATCCGAACTAGTTCC
GGGACTTTCTTGAGAGCCGACGAAGACACGACGCGGAGTTTGGAGCAAGT
TGAAGAGAAGATGGCGAAAGCAACCATGATACCTCGCGAGAATGGAGAGG
CTTTCAATGTGTTGAAGTACAATGTGGGACAAAAATACGACTGCCATTAT
GATGTTTTGACCCAGCTGAGTATGGACCTCAACCAAGCCAACGGATGGC
CTCCTTTCTCTTATATCTATCGGATGTGGAAGAGGGTGGAGAGACCATGT
TTCCCTTCGAAAATTTTCAAAACATGAACATAGGCTTTGACTACAAGAAG
TGCATTGGAATGAAAGTCAAGCCCCGCCAAGGTGATGCATTGCTTTTCTA
CTCAATGCATCCTAACGGCACATTTGATAAGAGCGCTCTGCATGGAAGCT
GCCCTGTAATCAAAGGCGAGAAATGGGTTGCCACAAAGTGGATTCGCAAC
ACTGACAAATTTTGATCACCACCATGCGAACGTTTTTACGTCCAAAATTA
GGACATAGGAATCTGTCAATCAAATTAAAGGACATATCTTTTATATCATT
TAAAAATTCTGAAACTGAGAACTCATATGAACACCAGTTGAAACATTCGG
GTCAACCGGATTATCGACAT Translation corresponding to P4H3cDNA
(SEQ ID NO. 6)
MPCPICVLSCAGMTLSLYNMKSSKNKGRKWNPFTYKLSLPQVLLWCTICL
LAGYAASNFFPQKIEEEAIYQPYRKSAQQEGEFPPGEFSEKVVLDHGSTG
DNFIADIPFQVLSWKPRALLYPRFASKEQCEAIMKLARTRLAPSALALRK
GESEDSTKDIRTSSGTFLRADEDTTRSLEQVEEKMAKATMIPRENGEAFN
VLKYNVGQKYDCHYDVFDPAEYGPQPSQRMASFLLYLSDVEEGGETMFPF
ENFQNMNIGFDYKKCIGMKVKPRQGDALLFYSMHPNGTFDKSALHGSCPV
IKGEKWVATKWIRNTDKF P4H4cDNA (Pp1s172_91V6.1 Accession No.:
XM_001774115; SEQ ID NO. 7)
GTTACACAAATTCATCAACCTCGAGGCATTTGGTTCATCAGTGGATCCAT
TTGTTGGGGTTTCGTGTGGATTGAGCTTGTGGGTTTCCTTCTCCGACTCG
GAAATCGCTCCTGACAGAGTTTTCACGGAAGCTTTTGAGGCTGGAAACGG
AGAAGGATTATTCCAAAGAATCGGTTTTTTAAAGTGTCACTTATCTTGTT
TTCAAGGACAGTCTCAATAACAATTTGGCGCAATTATCTGCAATGATTTA
CATGGATTGAATCGATTTTCAGTAGCTAAATGTAGGGTCTGCTAGGCCCT
CTATATTCCGACCCTTGAGTGAAGACACTGCCTCCCAGGCAGTCCGTGCC
TTATTTTAATCTCCTTGCGTGCAAAGAACAGGAAGGCTGACACCGATTAT
AAACGGTTGAGACATGAAAACGCCAAAGGTCCGGGCAAGGAGTGCAAACC
CTTTAAGATACAAGCTTGGTTTTCCTCTGGTGCTCTTGTGTTGCACATTC
TTCTTCTTGGTCGGCTTTTACGGTTCCAATTCCCTCTCAAGGAAGAAAA
ACATGTGGTGATTGACCCCGTCACCAATGAGAAACTTGTGTTCGAACATG
GCCGTACTGGAGACAGTTCTGTTACTGACATTCCTTTCCAGGTGTTAAGT

```
TGGAAACCACGTGCCCTTTTGTATCCGAATTTTGCAAGCAAAGAGCAATG
TGAAGCCATCATCAAGCTTGCGAGGACACGTCTTGCTCCTTCTGGTCTGG
CTTTGAGGAAAGGGGAGAGTGAAGCCACAACGAAAGAAATCAGAACTAGT
TCTGGAACTTTCTTGAGAGCCAGTGAAGATAAAACACAGAGTTTAGCGGA
GGTTGAGGAGAAGATGGCCAGAGCAACCATGATACCTCGGCAGAATGGGG
AGGCTTTTAATGTGTTGCGGTACAACCCAGGTCAAAAATACGATTGTCAC
TATGATGTTTTTGATCCAGCTGAGTATGGTCCTCAACCAAGCCAGCGGAT
GGCTTCCTTTCTCCTTTATTTATCAGACGTCGAAGAGGGCGGAGAAACGA
TGTTTCCCTTCGAAAACTTTCAAAATATGAACACAGGCTATAATTATAAG
GACTGTATTGGGTTGAAAGTGAAACCCCGCCAAGGCGATGCTCTTCTTTT
CTATTCAATGCATCCTAACGGTACATTTGACAAGACCGCATTGCATGGAA
GCTGTCCAGTTATCAAAGGCGAAAATGGGTCGCCACGAAGTGGATACGC
AATACCGACAAATTTTAATCTGAAAGATCCCACTGGTGACTGTTATAACT
TGCTGCCTTCTTAAAGTTCTTTCGGTAGTACTCTAGGAGCTTCAGGTTAT
CTTACAAAGTATCGGGTCTGAGAAAGTGTAAAATCTGTGCGTACCTGAA
TCCATCAATTAAGTCATGGGTGTTATCTTTTAACATTCCTGGTCTCTGCC
AACCAGAGTTCCAGAGAAACGGTTGTTCGCTGGATTATTGCCAGCTTAAA
GTTCACTTAAGAAATTCTAAACTCTTCAACTAAGAAGACATTGTCCTTG
```
Translation corresponding to P4H4cDNA
(SEQ ID NO. 8)
MKTPKVRARSANPLRYKLGFPLVLLCCTFFFLVGFYGSNSLSKEEKHVVI
DPVTNEKLVFEHGRTGDSSVTDIPFQVLSWKPRALLYPNFASKEQCEAII
KLARTRLAPSGLALRKGESEATTKEIRTSSGTFLRASEDKTQSLAEVEEK
MARATMIPRQNGEAFNVLRYNPGQKYDCHYDVFDPAEYGPQPSQRMASFL
LYLSDVEEGGETMFPFENFQNMNTGYNYKDCIGLKVKPRQGDALLFYSMH
PNGTFDKTALHGSCPVIKGEKWVATKWIRNTDKF P4H5cDNA (Pp1s12_247V6.1 Accession No.:
JX964782; SEQ ID NO. 9)
```
GCTGCTTCAGGGTAGGACAAACCATCGTCGAAGGGGATGTGGGTCGACCT
ATTTTGGTCAACTTTATCTGTCTTTCTACTTCCGATGAATTGCCGTTTTT
GTTGTAAGCGTTTGCACATGCAGGTTGGAGGCTGGTGAACTGCATACACA
AATTTGATAGTCGGGGAGAAAGAGGAGTTTCTCACAGTGTCTTTGGTGAT
TGGATCATCCTCGAGGAGCTTTTAGCTCGAAGGGTTTCCTGATTTTAAGT
TTGGAACCGAGGTATTTCAATCGTGAGAGTGGTTCTTAGCATGCATACAT
TTTGAGTGTGTAGGTATGGATCTCTATTCTAGAAGCCGTAGAGGCTGAGT
AACTATTGCATTCTCTGAAATCCTGTTTACCTCGGCGCGGCCACATCTCG
AAGTAGTCGGTAATTTTCTTCCTTGGGTTTCGTGGGAGCCGGGCGAAGTT
CGTAACTATGGCGAAGCTGAGTCGAGGTCAAAGGAGAGGAGCTGGCACGA
TGGCTTTGTTGGTGCTGGTCCTGTTGTCTCTAGCGCTCATGCTCATGTTG
GCACTTGGCTTTGTAGCCATGCCATCGGCGTCCCACGGGAGTTCGGCTGA
CGTTGTGGAAATCAAGCTGCCCTCACACAGGCATTTTGGTGCCAACCCCT
TATCACGTTGGGTTGAAGTCCTCTCTTGGGAGCCCAGAGCCTTTCTATAT
CACCACTTTCTGACAGAAGAGGAATGCAATCATCTAATTGAAGTGGCCAG
GCCAAGTCTGGTGAAGTCAACGGTTGTAGATAGTGATACAGGAAAGAGCA
AAGACAGCAGAGTACGCACAAGTTCAGGTACATTTTTGATGCGAGGCCAA
GATCCTGTGATCAAAAGAATCGAGAAGCGAATAGCTGACTTCACATTTAT
ACCTGCTGAGCAAGGTGAAGGCTTACAAGTTCTGCAGTACAAAGAAAGTG
AAAAATACGAGCCCCATTATGATTACTTCCACGATGCATACAATACCAAA
AATGGCGGCCAAAGAATTGCTACCGTACTGATGTACCTGTCAAATGTCGA
GGAAGGAGGAGAAACAGTTTTTCCAGCTGCTCAGGTGAACAAGACTGAAG
TTCCCGATTGGGATAAATTATCTGAGTGTGCTCAGAAAGGTCTTTCTGTG
CGACCACGCATGGGAGATGCCTTGCTTTTCTGGAGCATGAAACCAGATGC
GACACTTGATTCCACTAGCTTGCATGGTGGCTGCCCCGTGATCAAGGGTA
CCAAATGGTCTGCTACTAAGTGGTTACATGTAGAAAACTATGCAGCCTGA
TGAGGATGGTACAAGATGTCTTCTGCAGGAAGTGAATTGTCACAAGCACC
TGGTACAAGCAGATTCGAAATGCTTGGATGTAATGCATGGATGTTGGGAG
AGGACAAACATACAAATTTATGATTCTGCATTACGTGAGATGTAATGATG
AACCACCTCGTGCCTATCTGAATTCATATGAACAAACGAATAGATTTCCA
ATTCATACCAATAAAACAGAAAAGCCGCTTAACTTATTTGTTAACTTAGG
CAGTTTTTTTGTTTTATTATTGGTGGTTTGCAATCGACCTTAACGACCAT
TTCTTGTAATCACCACAAACAAGCAAATGCATATCTGATTTCATTCAAA
ATATACTTATAAAGACTGCTGAATCTATAACAAACAAAA
```
Translation corresponding to P4H5cDNA
(SEQ ID NO. 10)
MAKLSRGQRRGAGTMALLVLVLLSLALMLMLALGFVAMPSASHGSSADVV
EIKLPSHRHFGANPLSRWVEVLSWEPRAFLYHHFLTEEECNHLIEVARPS
LVKSTVVDSDTGKSKDSRVRTSSGTFLMRGQDPVIKRIEKRIADFTFIPA
EQGEGLQVLQYKESEKYEPHYDYFHDAYNTKNGGQRIATVLMYLSNVEEG
GETVFPAAQVNKTEVPDWDKLSECAQKGLSVRPRMGDALLFWSMKPDATL
DSTSLHGGCPVIKGTKWSATKWLHVENYAA P4H6_a_cDNA (Pp1s328_29V6.1 Accession No.:
JX964783; SEQ ID NO. 11)
```
GAAAAAGAGCAGCAGTTGGAGTTGGAGTAGGCCAGATCGATGCTCCTCCT
CCTCCCATGATGATAGATGACGAAGATTATGCTGTTGTTGTCGATGTTGT
TGCTCGCTGATCATCAACACGAAGTTGCCGTTGCAGCTGCTCTTGCTCTT
CACCGTCGACTCGGCAGAGGGGCACAGCTCAGCTGGTAATTTATTATTAG
TGCCCATGGGTGGATGGATGTGAGTGACATCGGCGCTTCTACCGACAGT
GTGAAACCCCAGCGAGGCTGTGCCTTGCCTTGCCTTGGCTTGTGTGCATT
GCCTCTCCCCTCCAGTTTTTGGTGGGTTGGTGTTTGTGTGAGGGGGGAA
CAGAGGAGAGGGCGGGGCAAGGGCTGTGGCAGCTATGGCGAGGTTGAGT
AGGGGGCAAAGGACTGGAGTTGGCACGATGGCATTGCTGGTGTTCGCGTT
TTTGTCTTTGATAGTCATGGTCATGTTGCTTCTGGACGTGGTAGCAATGC
CATCGGGACGTCGAGGCTCGATTGACGAGGGAGCCGAAGTGGAATTGAAG
CTGCCTACCCACAGGCATGTGGATGAAATCCACTGGCACCTTGGGTTGA
GGTCCTTTCCTGGGAGCCCAGAGCTTTTCTGTATCACCACTTTCTGACAC

```
AAGTGGAATGCAACCATCTTATTGAGGTGGCCAAGCCTAGCCTGGTGAAG

TCAACAGTTATAGATAGTGCTACGGGAAAAAGCAAAGACAGCAGGGTTCG

CACAAGTTCAGGGACATTTTTGGTGCGGGGCCAAGATCACATCATTAAGA

GGATTGAGAAACGTATCGCTGACTTCACATTCATACCTGTTGAACAAGGT

GAAGGCTTGCAAGTTTTGCAGTATAGAGAGAGTGAGAAATACGAGCCTCA

TTATGACTACTTTCACGATGCTTTCAATACTAAAAATGGTGGTCAGCGGA

TTGCTACCGTACTGATGTATCTGTCAGACGTTGAGAAAGGGGAGAAACA

GTTTTCCCGGCTTCTAAAGTGAACGCTAGTGAGGTTCCTGATTGGGATCA

GCGATCCGAATGCGCTAAACGGGGCCTTTCTGTACGACCACGTATGGGAG

ATGCCTTACTTTTTTGGAGCATGAAACCAGATGCGAAGCTTGACCCTACC

AGTTTGCATGGCGCTTGCCCTGTGATTCAAGGTACGAAATGGTCTGCTAC

AAAGTGGTTACATGTTGAAAAATACGCAGCACGGTAAACATCCTTCTAGA

AGTCTTCAACAGGATTACATGAATTATGCGAGCAGTCTTCTGGCATGAGC

AGAGGTGAACTTGCCCAAACTTGCTCATGGAACAACAGAATCAGCTTGCG

AGTTATTTACAAGGAGCGAGTGTCCATGCCTGAATGCTGGAACACCAGCG

TGATGAGAACGCTTAGGAATACCAATTCTTCACTGATTTTACAAACCACA

CTAGCTACTACACATGACAAATTTCATGCTTTGACTTGGTTGATCTGCTT

TTGTGTGAGGATCAGTATTTTATAAATAGGGGATGGAGCTCTTCAGCTCC

TAATGTGCGATTTCG

Translation corresponding to P4H6_a cDNA
(SEQ ID NO. 12)
MGGMDVSDIGASTDSVKPQRGCALPCLGLCALPLPSSFLVGWCLCEGGTE

ERAGARAVAAMARLSRGQRTGVGTMALLVFAFLSLIVMVMLLLDVVAMPS

GRRGSIDEGAEVELKLPTHRHVDENPLAPWVEVLSWEPRAFLYHHFLTQV

ECNHLIEVAKPSLVKSTVIDSATGKSKDSRVRTSSGTFLVRGQDHIIKRI

EKRIADFTFIPVEQGEGLQVLQYRESEKYEPHYDYFHDAFNTKNGGQRIA

TVLMYLSDVEKGGETVFPASKVNASEVPDWDQRSECAKRGLSVRPRMGDA

LLFWSMKPDAKLDPTSLHGACPVIQGTKWSATKWLHVEKYAAR

P4H6_b cDNA (Pp1s328_29V6.1 Accession No.:
JX964784; SEQ ID NO. 13)
GAAAAAGAGCAGCAGTTGGAGTTGGAGTAGGCCAGATCGATGCTCCTCCT

CCTCCCATGATGATAGATGACGAAGATTATGCTGTTGTTGTCGATGTTGT

TGCTCGCTGATCATCAACACGAAGTTGCCGTTGCAGCTGCTCTTGCTCTT

CACCGTCGACTCGGCAGAGGGGCACAGCTCAGCTGGTAATTTATTATTAG

TGCCCATGGGTGGGATGGATGTGAGTGACATCGGCGCTTCTACCGACAGT

GTGAAACCCCAGCGAGGCTGTGCCTTGCCTTGCCTTGGCTTGTGTGCATT

GCCTCTCCCCTCCAGTCGTAATTGAGACGTACTATTAAACACGTAGGCGG

TAGTTTTTGGTGGGTTGGTGTTTGTGTGAGGGGGAACAGAGGAGAGGGC

GGGGGCAAGGGCTGTGGCAGCTATGGCGAGGTTGAGTAGGGGCAAAGGA

CTGGAGTTGGCACGATGGCATTGCTGGTGTTCGCGTTTTTGTCTTTGATA

GTCATGGTCATGTTGCTTCTGGACGTGGTAGCAATGCCATCGGGACGTCG

AGGCTCGATTGACGAGGGAGCCGAAGTGGAATTGAAGCTGCCTACCCACA

GGCATGTGGATGAAAATCCACTGGCACCTTGGGTTGAGGTCCTTTCCTGG

GAGCCCAGAGCTTTTCTGTATCACCACTTTCTGACACAAGTGGAATGCAA

CCATCTTATTGAGGTGGCCAAGCCTAGCCTGGTGAAGTCAACAGTTATAG

ATAGTGCTACGGGAAAAAGCAAAGACAGCAGGGTTCGCACAAGTTCAGGG

ACATTTTTGGTGCGGGGCCAAGATCACATCATTAAGAGGATTGAGAAACG

TATCGCTGACTTCACATTCATACCTGTTGAACAAGGTGAAGGCTTGCAAG

TTTTGCAGTATAGAGAGAGTGAGAAATACGAGCCTCATTATGACTACTTT

CACGATGCTTTCAATACTAAAAATGGTGGTCAGCGGATTGCTACCGTACT

GATGTATCTGTCAGACGTTGAGAAGGGGGAGAAACAGTTTTCCCGGCTT

CTAAAGTGAACGCTAGTGAGGTTCCTGATTGGGATCAGCGATCCGAATGC

GCTAAACGGGGCCTTTCTGTACGACCACGTATGGGAGATGCCTTACTTTT

TTGGAGCATGAAACCAGATGCGAAGCTTGACCCTACCAGTTTGCATGGCG

CTTGCCCTGTGATTCAAGGTACGAAATGGTCTGCTACAAAGTGGTTACAT

GTTGAAAAATACGCAGCACGGTAAACATCCTTCTAGAAGTCTTCAACAGG

ATTACATGAATTATGCGAGCAGTCTTCTGGCATGAGCAGAGGTGAACTTG

CCCAAACTTGCTCATGGAACAACAGAATCAGCTTGCGAGTTATTTACAAG

GAGCGAGTGTCCATGCCTGAATGCTGGAACACCAGCGTGATGAGAACGCT

TAGGAATACCAATTCTTCACTGATTTTACAAACCACACTAGCTACTACAC

ATGACAAATTTCATGCTTTGACTTGGTTGATCTGCTTTTGTGTGAGGATC

AGTATTTTATAAATAGGGGATGGAGCTCTTCAGCTCCTAATGTGCGATTT

CG

Translation corresponding to P4H6_b cDNA
(SEQ ID NO. 14)
MARLSRGQRTGVGTMALLVFAFLSLIVMVMLLLDVVAMPSGRRGSIDEGA

EVELKLPTHRHVDENPLAPWVEVLSWEPRAFLYHHFLTQVECNHLIEVAK

PSLVKSTVIDSATGKSKDSRVRTSSGTFLVRGQDHIIKRIEKRIADFTFI

PVEQGEGLQVLQYRESEKYEPHYDYFHDAFNTKNGGQRIATVLMYLSDVE

KGGETVFPASKVNASEVPDWDQRSECAKRGLSVRPRMGDALLFWSMKPDA

KLDPTSLHGACPVIQGTKWSATKWLHVEKYAAR
```

All deduced protein sequences had a prolyl-4-hydroxylase alpha subunit catalytic domain (SMART 0702). N-terminal transmembrane domains were predicted for all homologues except P4H2 (TMHMM server v.2.0, www.cbs.dtu.dk).

In order to gain more information about the predicted P4H enzymes, the deduced amino acid sequences were aligned with sequences of already characterized P4Hs from human, *Arabidopsis thaliana* and *Nicotiana tabacum*. Protein sequence alignments were performed with the program CLUSTAL W (ebi.ac.uk) and visualized with Jalview (www.jalview.org). The catalytic domain in the C-terminal end of the protein is highly conserved in all seven *P. patens* homologues (FIG. 1). The seven putative P4Hs share 16-24% identity with the human catalytic a (I) subunit and 30-63% identity with AtP4H1. Among the moss sequences the degree of identity is between 30 and 81%. All sequences contain the motif HXD and a distal histidine, which are necessary to bind the cofactor $Fe^{2+}$. Further, they contain the basic residue lysine which binds the C-5 carboxyl group of 2-oxoglutarate (FIG. 1). These residues are indispensable for the activity of collagen P4Hs (Kivirikko and Myllyharju, Matrix Biol., 16:357-368, 1998) and of P4H1 from *A. thaliana* (Hieta and Myllyharju, J. Biol. Chem., 277:23965-23971, 2002), indicating that all seven sequences from *P. patens* are functional prolyl-4-hydroxylases.

Experiment 2: In Silico Prediction of Intracellular Localization

Recombinant human erythropoietin (rhEPO) serves as an example of a recombinant human protein in the following examples. Non-human prolyl-hydroxylation occurred on moss-derived rhEPO which has been secreted from the tissue to the medium of the moss bioreactor culture. Therefore, it was concluded that the P4H enzyme responsible for posttranslational rhEPO modification is located in the secretory compartments, i.e. the endoplasmic reticulum (ER) or the Golgi apparatus. Accordingly, the subcellular localization of the seven *P. patens* P4H homologues was examined. First, their putative intracellular localization was analyzed in silico with four different programs based on different algorithms: Target P (www.cbs.dtu.dk), MultiLoc (abi.inf.uni-tuebingen.de), SherLoc (abi.inf.uni-tuebingen.de) and Wolf PSORT (wolfpsort.org). No consistent prediction was obtained by this approach (Table 1).

clear indication of a specific P4H responsible for generation of Hyp on secreted rhEPO in *P. patens*.

Figure 3:
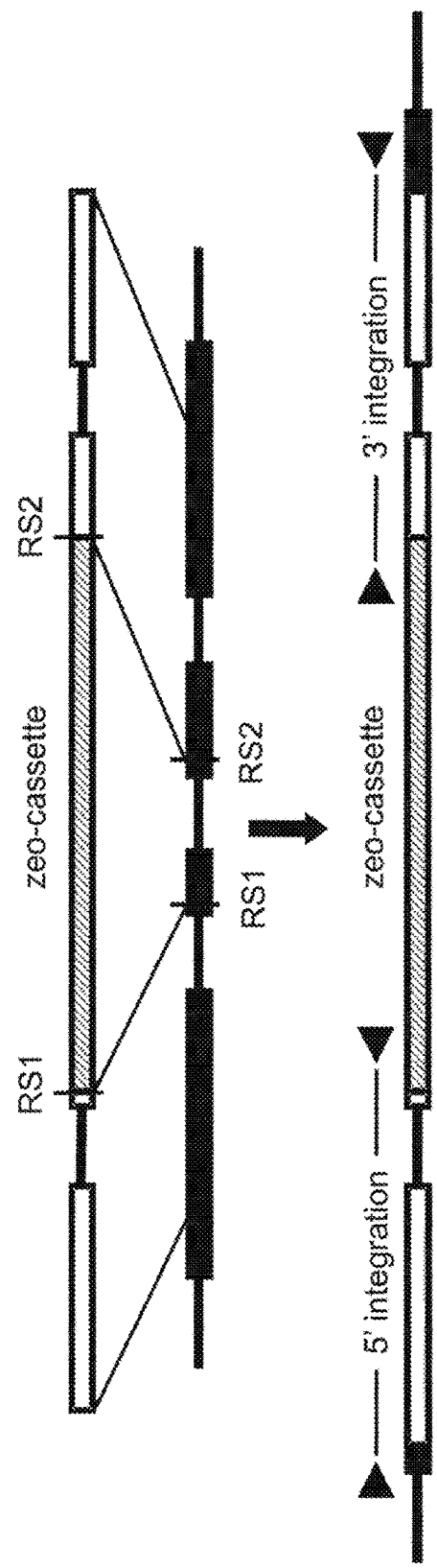
FIG. 3 Schematic representation of the p4h knockout constructs

Experiment 4: Ablation of the Gene Functions of Each of the *P. patens* P4H Homologues In order to definitively identify those homologues responsible for plant-typical prolyl-hydroxylation of moss-produced rhEPO the gene functions of each of the *P. patens* P4H homologues were ablated. Accordingly, gene-targeting constructs for the six p4h genes were designed (FIG. 3).

The gene targeting constructs were then transferred to the rhEPO-producing moss line 174.16 (Weise et al., Plant Biotechnol. J., 5:389-401, 2007) to generate specific knockout (KO) lines for each of the P4H-genes. After antibiotic selection, surviving plants were screened for homologous integration of the KO construct into the correct genomic locus (for details on the screening of transformed plants, see below).

Loss of the respective transcript was proven by RT-PCR (FIG. 4a), confirming successful gene ablation. One line for each genetic modification was chosen for further analysis, and stored in the International Moss Stock Center (moss-stock-center.org; Table 2).

TABLE 1

In silico localization prediction of *Physcomitrella patens* P4Hs using different programs.

| P4H | P4H1 | P4H2 | P4H3 | P4H4 | P4H5 | P4H6a | P4H6b |
|---|---|---|---|---|---|---|---|
| SherLok | ER | ER | ER | Golgi | ER | secreted | mitochondria |
| WoLFPSORT | vacuole | plastid | plastid | nucleus | vacuole | cytoplasm | plastid |
| MultiLoc | mitochondria | plastid | plastid | mitochondria | mitochondria | plastid | mitochondria |
| Target p | SP | / | / | mitochondria | mitochondria | mitochondria | mitochondria |

Experiment 3: In Vivo Analysis of Intracellular Localization

The in vivo intracellular localization of each of the seven *P. patens* P4Hs was studied by expressing them as GFP fusion proteins (green fluorescent protein, P4H-GFP) in *P. patens* cells (for details on the generation of plasmids and on the plant material and transformation procedure, see below). Subcellular localization of the seven different P4H-GFP fusion proteins was analyzed 3 to 14 days after transfection by Confocal Laser Scanning Microscopy (CLSM) (510 META; Carl Zeiss MicroImaging, Jena, Germany) and the corresponding software (version 3.5). Excitation at 488 nm was achieved with an argon laser and emission was measured with a META detector at 494-558 nm for GFP and at 601-719 nm for the chlorophyll. Cells were examined with a C-Apochromat 63x/1.2 W corr water immersion objective (Carl Zeiss MicroImaging). Confocal planes were exported from the ZEN2010 software (Carl Zeiss MicroImaging).

In optical sections GFP signals from all seven different P4H fusion proteins were predominantly detected as defined circular structures around the nucleus, revealing labeling of the nuclear membranes (FIG. 2). As the nuclear membrane is part of the endomembrane continuum of eukaryotic cells, these signals reveal that all seven moss P4Hs were targeted to the secretory compartments. An ER-targeted GFP version (ASP-GFP-KDEL, Schaaf et al., Eur. J. Cell Biol., 83:145-152, 2004) as well as GFP without any signal peptide displaying GFP fluorescence in the cytoplasm as well as the nucleus (Schaaf et al., Eur. J. Cell Biol., 83:145-152, 2004) served as controls. Thus, these experiments provided no

TABLE 2

International Moss Stock Center accession numbers of plants used.

| Plants | IMSC No. |
|---|---|
| EPO 174.16 | 40216 |
| p4h1KO No. 192 EPO | 40218 |
| p4h2 KO No. 6 EPO | 40234 |
| p4h3 KO No. 21 EPO | 40230 |
| p4h4 KO No. 95 EPO | 40231 |
| p4h5 KO No. 29 EPO | 40223 |
| p4h6 KO No. 31 EPO | 40239 |
| p4h1 OE No. 12 in p4h1 KO 192 EPO | 40336 |
| p4h1 OE No. 16 in p4h1 KO 192 EPO | 40337 |
| p4h1 OE No. 32 in p4h1 KO 192 EPO | 40338 |
| p4h1 OE No. 41 in p4h1 KO 192 EPO | 40339 |
| p4h1 OE No. 45 in p4h1 KO- 192 EPO | 40340 |

Experiment 5: Analysis of the Recombinant Proteins Via Mass Spectrometry

To investigate the effect of each of the p4h ablations on the prolyl-hydroxylation observed for moss-produced rhEPO, the recombinant protein from each of the KO lines (Δp4h) was analyzed via mass spectrometry. For this purpose, total soluble proteins were precipitated from the culture supernatant of the parental plant 174.16 and one knockout line from each p4h homologue, and separated by SDS-PAGE. Subsequently, the main rhEPO-containing band was cut from the Coomassie-stained gel, digested with trypsin and subjected to mass spectrometry for an analysis of the tryptic peptide EAISPPDAASAAPLR (144-158; SEQ ID NO. 81) (for details on protein and peptide analysis, see below). In the parental plant 174.16, almost half of the rhEPO was hydroxylated (FIG. 5), mainly in the second proline from the SPP motif, as shown by MS/MS (FIG. 6). Surprisingly, while rhEPO produced in moss lines with ablated p4h2, p4h3, p4h4, p4h5 or p4h6, respectively, was hydroxylated in similar levels to those found on the parental plant, the ablation of exclusively the p4h1 gene was sufficient to completely abolish the prolyl-hydroxylation on the biopharmaceutical (FIG. 5). Growth rate, rhEPO productivity and secretion of the protein to the culture medium were not impaired in these knockout plants compared to the parental line 174.16 (data not shown). Thus, the complete lack of Hyp on rhEPO produced by the Δp4h1 lines was shown.

It is to be noted that neither sequence analysis nor intracellular localization of the seven proteins revealed which genes were responsible for the adverse O-glycosylation of rhEPO. Only the ablation of each of the seven genes revealed surprisingly the responsible gene.

Experiment 6: Verification of P4H1 Enzymatic Activity

To verify P4H1 enzymatic activity in prolyl-hydroxylation this gene was ectopically expressed in the Δp4h1 knockout line #192. Strong overexpression of the p4h1 transcript was confirmed in the resulting lines via semi-quantitative RT-PCR (FIG. 4b). Five p4h1 overexpression lines (p4h1OE) were analyzed for rhEPO-Pro-hydroxylation. The LC-ESI-MS results revealed that p4h1 overexpression restored prolyl-hydroxylation of the moss-produced rhEPO (FIG. 7). The proportion of hydroxylated rhEPO, as well as the hydroxylation pattern, was altered by the elevated expression levels of the gene. While in the parental plant 174.16, with native P4H1 activity, approximately half of rhEPO displayed Hyp (FIG. 5), nearly all rhEPO was oxidized in the p4h1 overexpressors (FIG. 7). Furthermore, in these overexpressors not only one proline in the motif SPP was hydroxylated as seen in the parental plant 174.16, but both contiguous prolines were converted to Hyp (FIG. 7). Thus, it was shown that the expression of p4h1 is essential and sufficient for the prolyl-hydroxylation of the moss-produced rhEPO, and that its expression level influences its enzyme activity, not only in the proportion of hydroxylated protein molecules but also in the pattern of hydroxylation.

Experiment 7: Analysis of the rhEPO N-Terminal Peptide APPRLICDSRVL (SEQ ID NO. 82) for Prolyl-Hydroxylation in P. patens As hydroxylation and arabinosylation of the human epithelial mucin MUC1 at the sequence APP was reported upon expression in N. benthamiana (Pinkhasov et al., Plant Biotechnol. J., 9:991-1001, 2011), the rhEPO N-terminal peptide APPRLICDSRVL was analyzed for prolyl-hydroxylation in P. patens. After chymotryptic digestion of rhEPO derived from the parental plant 174.16, the knockout plant p4h1 #192 and the overexpressor p4h1OE-451, LC-ESI-MS analysis revealed that this peptide was not hydroxylated in any of the cases (FIG. 8), demonstrating that the mere presence of contiguous proline residues preceded by an alanine is not sufficient to be recognized by moss prolyl-hydroxylases.

Figure 9:
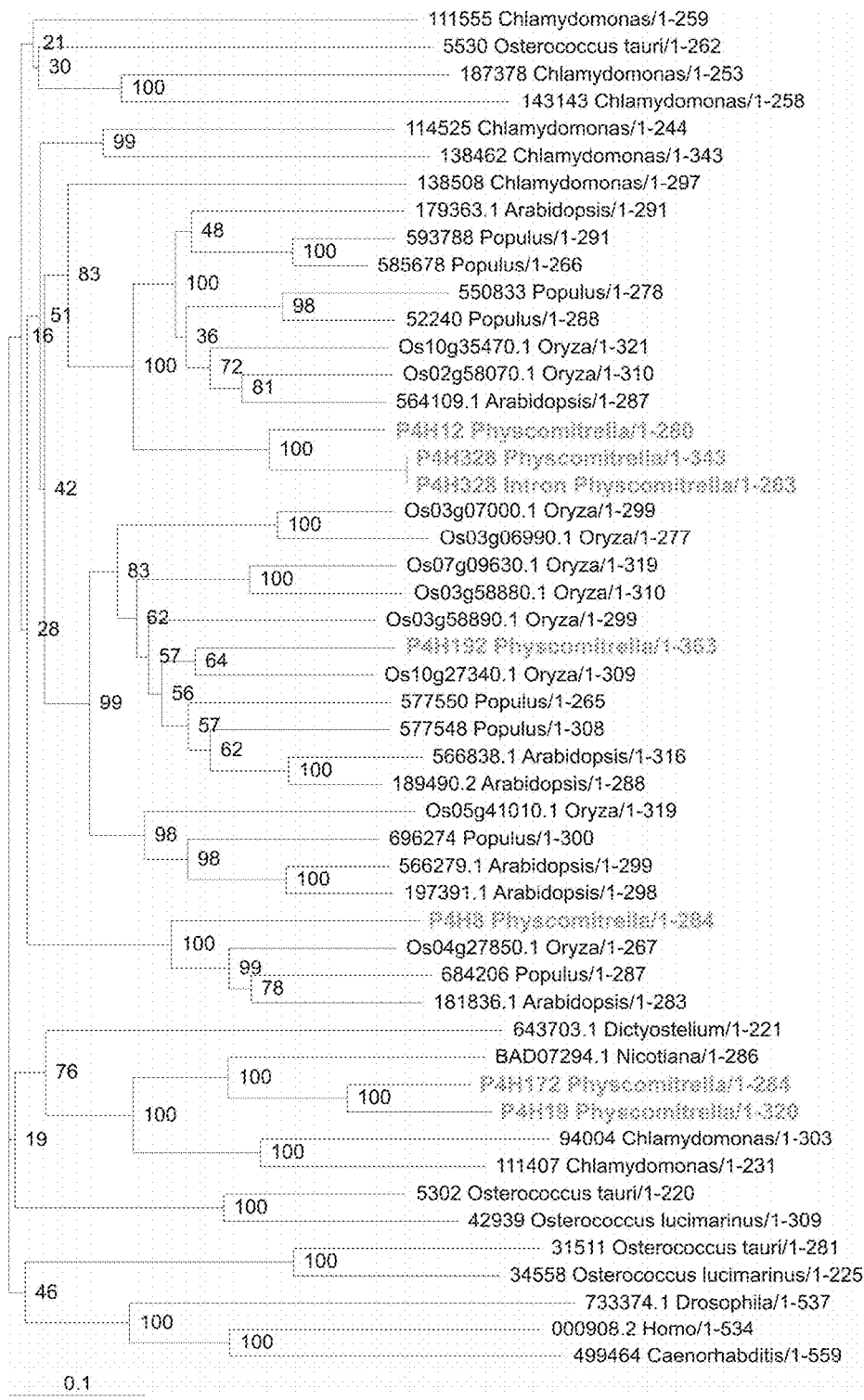

Experiment 8: Phylogenetic Comparison of the Sequences of Plant Prolyl-4-Hydroxylases A multiple sequence alignment was generated from the amino acid sequences of the prolyl-4-hydroxylases of different plants (e. g., Populus, Oryza, Arabidopsis, Physcomitrella) by using the program Jalview (MAFFT Version 5.0). A phylogenetic tree was calculated with QuickTree (Howe et al., Bioinformatics, 18:1546-1547, 2002). The phylogenetic tree is shown in FIG. 9.

Methods Relating to Above Experiments
Generation of Plasmid Constructs

The cDNAs corresponding to the seven P4H homologues identified in Physcomitrella patens were amplified using the primers listed in Table 3 (see below).

The cDNAs were cloned into pJET 1.2 (CloneJET™ PCR CloningKit, Fermentas, St Leon-Rot, Germany). Subsequently, the p4h coding sequences including a portion of the 5' UTR were cloned into the plasmid mAV4mcs (Schaaf et al., Eur. J. Cell Biol., 83:145-152, 2004) using the XhoI and BglII sites giving rise to N-terminal fusion P4H-GFP proteins under the control of the cauliflower mosaic virus (CaMV) 35S promoter. Unmodified mAV4mcs was used as a control for cytoplasmic and nuclear localization. As positive control for ER localization, pASP-GFP-KDEL was taken (Schaaf et al., Eur. J. Cell Biol., 83:145-152, 2004).

To generate the p4h knockout constructs, P. patens genomic DNA fragments corresponding to the prolyl-4-hydroxylases were amplified using the primers listed in Table 3 and cloned either into pCR®4-TOPO® (Invitrogen, Karlsruhe, Germany) or into pETBlue-1 AccepTor™ (Novagen, Merck KGaA, Darmstadt, Germany). The pTOPO_p4h1 genomic fragment was first linearized using BstBI and SacI, thus deleting a 273 bp fragment, and recircularized by ligating double-stranded oligonucleotide containing restriction sites for BamHI and HindIII. These sites were used for the insertion of a zeomycin resistance cassette (zeo-cassette). The zeo-cassette was obtained from pUC-zeo (Parsons et al., Plant Biotechnol. J., 10:851-861, 2012) by digestion with HindIII and BamHI. For the p4h5 KO construct, a 1487 bp fragment was cut out from the pTOPO_p4h5 using SalI and BglII sites and replaced by double-stranded oligonucleotide containing restriction sites for BamHI and HindIII. These restriction sites were used for the insertion of the zeo-cassette obtained from the pUC-Zeo plasmid. The p4h2 KO construct was cloned into the pET-Blue-1 AccepTor™, and the zeo-cassette replaced a 270 bp genomic fragment deleted by digestion with KpnI and HindIII. The zeo-cassette obtained from pRT101-zeo (Parsons et al., Plant Biotechnol. J., 10:851-861, 2012) by HindIII digestion was inserted into the pET_p4h3 and the pTOPO_p4h4 KO constructs digested with the same enzyme, replacing a 990 bp and a 1183 bp genomic fragment, respectively. For the p4h6 KO construct, the zeo-cassette was obtained from the pUC-zeo via digestion with HindIII and SacI and inserted into pTOPO_p4h6, replacing a 1326 bp genomic fragment. In all KO constructs the regions homologous to the target gene had approximately the same size at both ends of the selection cassette, comprising between 500 and 1000 bp.

For the overexpression construct, the p4h1 coding sequence and 79 bp of the 5'UTR were amplified from moss WT cDNA with the primers listed in Table 3, and cloned under the control of the 35S promoter and the nos terminator into the mAV4mcs vector (Schaaf et al., Eur. J. Cell Biol., 83:145-152, 2004). For this purpose the GFP gene was deleted from the vector by digestion with Ecl136II and SmaI and subsequent relegation of the vector. The p4h1 cDNA was inserted into the vector via XhoI and BglII restriction sites. The p4h1 overexpression construct was linearized via digestion with EcoRI and PstI and transferred into the line Δp4h1 No. 192 together with pUC 18 sul (Parsons et al., Plant Biotechnol. J., 10:851-861, 2012) for sulfadiazine selection.

TABLE 3

Oligonucleotides used and corresponding NOs.

| gene | | oligonucleotide | SEQ ID NO. |
|---|---|---|---|
| | | P4H-GFP construct | |
| p4h1 | | fwd: 5'-GGGATGGAGTAATTCTACGAAGC-3' | 15 |
| | | rev: 5'-AATCAAAGGCTCGCTGCCTCAT-3' | 16 |
| p4h2 | | fwd: 5'-GTGATGCGTGATCCTGTGC-3' | 17 |
| | | rev: 5'-GGCACACATGGCATGCTTTC-3' | 18 |
| p4h3 | | fwd: 5'-GGTGTTATGTAGAGATTCGTCACAAC-3' | 19 |
| | | rev: 5'-GAAATTTGTCAGTGTTGCGAATC-3' | 20 |
| p4h4 | | fwd: 5'-GACTCGGAAATCGCTCCTGA-3' | 21 |
| | | rev: 5'-GAAATTTGTCGGTATTGCGTATC-3' | 22 |
| p4h5 | | fwd: 5'-GCCACATCTCGAAGTAGTCGGTAAT-3' | 23 |
| | | rev: 5'-CGGCTGCATAGTTTTCTACATGTAAC-3' | 24 |
| p4h6-a | | fwd: 5'-CTCTTGCTCTTCACCGTCGACTC-3' | 25 |
| | | rev: 5'-ACCGTGCTGCGTATTTTTCAAC-3' | 26 |
| p4h6-b | | fwd: 5'-GAGACGTACTATTAAACACGTAGG-3' | 27 |
| | | rev: 5'-ACCGTGCTGCGTATTTTTCAAC-3' | 28 |
| | | genomic DNA amplification for KO construct | |
| p4h1 | | fwd: 5'-TGAATTCTGAATGTCATAAGGCCTCTACTG-3' | 29 |
| | | rev: 5'-TGAATTCAGAGGGTAGGATTGTGTGAAG-3' | 30 |
| p4h2 | | fwd: 5'-CGAATTCCTCTGCTCCCTGTTCTTGTTTG-3' | 31 |
| | | rev: 5'-CGAATTCCACAAACTTCATCGACTTGATCC-3' | 32 |
| p4h3 | | fwd: 5'-GAATTCGTTGCAGTAATCCTTGGTGAT-3' | 33 |
| | | rev: 5'-GAATTCTCTCCACCCTCTTCCACATC-3' | 34 |
| p4h4 | | fwd: 5'-TGAATTCCTGAGGGGATTGAAGAG-3' | 35 |
| | | rev: 5'-TGAATTCAGAACACAGGGATCAGC-3' | 36 |
| p4h5 | | fwd: 5'-TGAATTCTGCAGCTTGTTACACTCCCAAT-3' | 37 |
| | | rev: 5'-ATGAATTCAGATAGGCACGAGGTGGT-3' | 38 |
| p4h6 | | fwd: 5'-TGAATTCTGCAGTAGATGGCCAATCATGT-3' | 39 |
| | | rev: 5'-GTAATCCTGCAACAAGAATTCAAAGCAG-3' | 40 |
| | | screening of integration in the genome | |
| p4h1 | 5'-integration | fwd: 5'-GGCTAATGATGAAGATGCGAGA-3' | 41 |
| | | rev: 5'-TGTCGTGCTCCACCATGTTG-3' | 42 |
| | 3'-integration | fwd: 5'-GTTGAGCATATAAGAAACCC-3' | 43 |
| | | rev: 5'-AGCATCCCCTCGTTTAGGTT-3' | 44 |
| p4h2 | 5'-integration | fwd: 5'-TGTGGTATTCTCGCAGATTAGGG-3' | 45 |
| | | rev: 5'-TGTCGTGCTCCACCATGTTG-3' | 46 |
| | 3'-integration | fwd: 5'-GTTGAGCATATAAGAAACCC-3' | 47 |
| | | rev: 5'-CGGTCATAATTTGAGTTTTGCT-3' | 48 |
| p4h3 | 5'-integration | fwd: 5'-CAACGGATGCCATTGACAGT-3' | 49 |
| | | rev: 5'-TGTCGTGCTCCACCATGTTG-3' | 50 |
| | 3'-integration | fwd: 5'-GTTGAGCATATAAGAAACCC-3' | 51 |
| | | rev: 5'-CATTTGGCAACTTAAGGGTGTA-3' | 52 |

TABLE 3-continued

Oligonucleotides used and corresponding NOs.

| gene | oligonucleotide | | SEQ ID NO. |
|---|---|---|---|
| p4h4 | 5'-integration | fwd: 5'-GACTCGGAAATCGCTCCTGA-3' | 53 |
| | | rev: 5'-TGTCGTGCTCCACCATGTTG-3' | 54 |
| | 3'-integration | fwd: 5'-GTTGAGCATATAAGAAACCC-3' | 55 |
| | | rev: 5'-CATCGACAGTTGTTCGTGGA-3' | 56 |
| p4h5 | 5'-integration | fwd: 5'-GTAAAGGACATTCGTTTATGCATCG-3' | 57 |
| | | rev: 5'-TGTCGTGCTCCACCATGTTG-3' | 58 |
| | 3'-integration | fwd: 5'-GTTGAGCATATAAGAAACCC-3' | 59 |
| | | rev: 5'-TGTGGTGATTACAAGAAATGGTCGT-3' | 60 |
| p4h6 | 5'-integration | fwd: 5'-ATAGGTGTCGCTACAGCAATCG-3' | 61 |
| | | rev: 5'-TGTCGTGCTCCACCATGTTG-3' | 62 |
| | 3'-integration | fwd: 5'-GTTGAGCATATAAGAAACCC-3' | 63 |
| | | rev: 5'-ATGGACACTCGCTCCTTGTAA-3' | 64 |
| p4h1 | overexpression | fwd: 5'-GGGATGGAGTAATTCTACGAAG-3' | 65 |
| | | rev: 5'-CTAATCAAAGGCTCGCTGCCTCAT-3' | 66 |
| | transcript screening | | |
| p4h1 | | fwd: 5'-GGCTAATGATGAAGATGCGAGA-3' | 67 |
| | | rev: 5'-AGCATCCCCTCGTTTAGGTT-3' | 68 |
| p4h2 | | fwd: 5'-AGGACAAGCTGGAGAAGTCAATG-3' | 69 |
| | | rev: 5'-GCCTAGCACACATGGCATG-3' | 70 |
| p4h3 | | fwd: 5'-GGTGTTATGTAGAGATTCGTCACAAC-3' | 71 |
| | | rev: 5'-GAATTCTCTCCACCCTCTTCCACATC-3' | 72 |
| p4h4 | | fwd: 5'-TTGGTCGGCTTTTACGGTTC-3' | 73 |
| | | rev: 5'-AAAGAAGAGCATCGCCTTGG-3' | 74 |
| p4h5 | | fwd: 5'-TCCTGTTGTCTCTAGCGCTCAT-3' | 75 |
| | | rev: 5'-CGGCTGCATAGTTTTCTACATGTAAC-3' | 76 |
| p4h6 | | fwd: 5'-CCAGAGCTTTTCTGTATCACCAC-3' | 77 |
| | | rev: 5'-ACCGTGCTGCGTATTTTTCAAC-3' | 78 |
| tbp | | fwd: 5'-GCTGAGGCAGTCTTGGAG-3' | 79 |
| | | rev: 5'-TCGAGCCGGATAGGGAAC-3' | 80 |

Plant Material and Transformation Procedure

*Physcomitrella patens* (Hedw.) Bruch & Schimp was cultivated as described previously (Frank et al., Plant Biol., 7:220-227, 2005). Moss-produced rhEPO was shown to be hydroxylated at the prolyl-hydroxylation consensus motif SPP (amino acids 147-149), therefore the rhEPO-producing *P. patens* line 174.16 (Weise et al., Plant Biotechnol. J., 5:389-401, 2007) was used as the parental line for the p4h knockout generation and the line Δp4h1 #192 was used for the generation of p4h1 overexpression lines. In these moss lines the α1,3 fucosyltransferase and the β1,2 xylosyltransferase genes are disrupted (Koprivova et al., Plant Biotechnol. J., 2:517-523, 2004). Wild-type moss was used for the subcellular localization experiments with P4H-GFP.

Protoplast isolation and PEG-mediated transfection was performed as described previously (Frank et al., Plant Biol., 7:220-227, 2005; Rother et al., J. Plant Physiol., 143:72-77, 1994). Mutant selection was performed with Zeocin™ (Invitrogen) or sulfadiazine (Sigma) as described before (Parsons et al., Plant Biotechnol. J., 10:851-861, 2012).

For rhEPO production, *P. patens* was cultivated as described before (Parsons et al., Plant Biotechnol. J., 10:851-861, 2012).

Screening of Transformed Plants

Screening of stable transformed plants was performed via direct PCR (Schween et al., Plant Mol. Biol. Rep., 20:43-47, 2002) with genomic DNA extracted as described before (Parsons et al., Plant Biotechnol. J., 10:851-861, 2012). From these extracts, 2 µl were used as template for PCR, using the primers listed in Table 3 to check the 5' and 3' integration of the knockout construct in the correct genomic locus and to check the integration of the overexpression construct into the moss genome, respectively. Plants, which showed the expected PCR, products were considered as putative knockouts or overexpression lines, respectively, and subsequently analyzed. The absence of the p4h transcripts in the KO lines was analyzed via RT-PCR as described before (Parsons et al., Plant Biotechnol. J., 10:851-861, 2012) using the primers listed in Table 3. Expression of p4h1 in the overexpression lines was analyzed via semi-quantitative RT-PCR. For this purpose, cDNA equivalent to 150 ng RNA was amplified with 24, 26 and 28 cycles using the p4h1 primers listed in Table 3. The primers for the constitutively expressed TATA box-binding protein, TBP fwd and TBP rev (Table 3) were used as controls.

Protein and Peptide Analysis

Total soluble proteins were recovered from 160 ml of a 16-days-old culture supernatant by precipitation with 10% (w/v) trichloroacetic acid (TCA, Sigma-Aldrich, Deisenhofen, Germany) as described (Büttner-Mainik et al., Plant Biotechnol. J., 9:373-383, 2011). The pellet was resuspended in sample Laemmli loading buffer (Biorad, Munich, Germany) and electrophoretic separation of proteins was carried out in 12% SDS-polyacrylamide gels (Ready Gel Tris-HCl, BioRad) at 150 V for 1 h under non-reducing conditions.

For peptide analysis, the proteins in the gels were stained with PageBlue® Protein Staining Solution (Fermentas) and the bands corresponding to 25 kDa were cut out, 5-alkylated and digested with trypsin or chymotrypsin (Grass et al., Anal. Bioanal. Chem. 400:2427-2438, 2011). Analysis by reversed-phase liquid chromatography coupled to electrospray ionization mass spectrometry on a Q-TOF instrument (LC-ESI-MS and MS/MS) was performed as described previously (Grass et al., Anal. Bioanal. Chem. 400:2427-2438, 2011).

Quantification of the moss-produced rhEPO was performed using a hEPO Quantikine IVD ELISA kit (cat. no DEP00, R&D Systems) according to the manufacturer's protocol.

DETAILED DESCRIPTION OF THE FIGURES

FIG. 1 shows the protein sequence comparison of *P. patens* putative prolyl-4-hydroxylases (P4Hs): PpP4H1 (SEQ ID No: 2), PpP4H6a (SEQ ID No: 12), PpP4H6b (SEQ ID No: 14), PpP4H5 (SEQ ID No: 10), PpP4H2 (SEQ ID No: 4), PpP4H3 (SEQ ID No: 6), PpP4H4 (SEQ ID No: 8). Amino acids that are identical in at least 5 sequences are marked with dashes above the respective positions. The conserved residues responsible for binding $Fe^{2+}$ and the C-5 carboxyl group of 2-oxoglutarate are marked with asterisk below the respective positions. The first 147 amino acids of the human α (I) subunit did not align with any other analyzed sequence.

FIG. 2 shows the in vivo subcellular localization of *P. patens* P4H homologues. Fluorescence of P4H-GFP fusion proteins in *P. patens* protoplasts was observed by confocal microscopy 3 to 14 days after transfection. The images obtained for PpP4H1-GFP, PpP4H3-GFP and PpP4H4-GFP are taken as example of the fluorescence pattern which was observed for all homologues. (a-c) PpP4H1-GFP, (d-f) PpP4H3-GFP, (g-i) PpP4H4-GFP, (j-l) ASP-GFP-KDEL as control for ER localization, (m-o) GFP without any signal peptide as control for cytosolic localization. (a, d, g, j and m) single optical sections emitting GFP fluorescence (494-558 nm), (b, e, h, k and n) merge of chlorophyll autofluorescence (601-719 nm) and GFP flourescence, (c, f, i, l and o) transmitted light images. The arrows indicate the cell nucleus membrane.

FIG. 3 shows the schematic representation of the p4h knockout constructs. Exons are presented as rectangles and introns as lines. White rectangles represent the regions of the genes used for the constructs and striped rectangles represent the selection cassette. The restriction sites used to insert the selection cassette are marked as RS. Arrows represent oligonucleotides used for the screening of genomic integration.

Figure 4A:
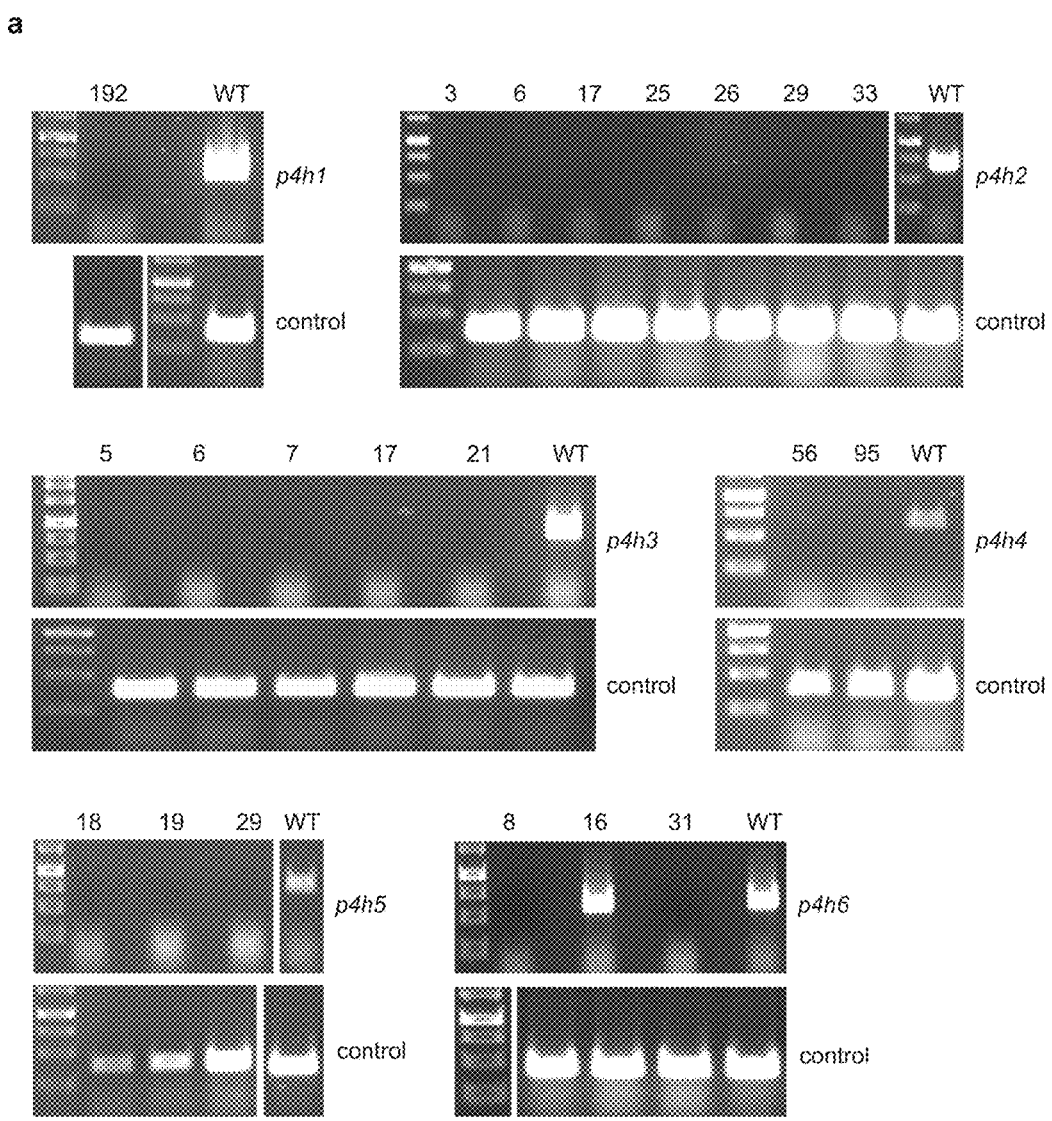
FIG. 4 p4h gene expression analysis in recombinant moss lines
Figure 4B:
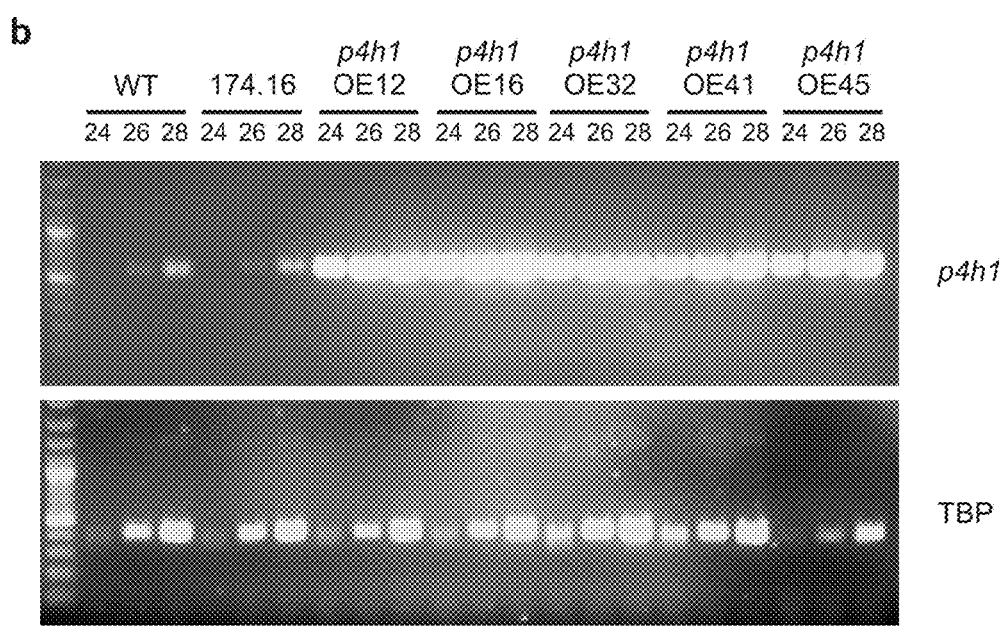

FIGS. 4a and 4b show the p4h gene expression analysis in recombinant moss lines. FIG. 4a is the expression analysis of p4h1, p4h2, p4h3, p4h4, p4h5 and p4h6, respectively, in the putative knock-out plants. As a control for efficient mRNA isolation, RT-PCR was performed with primers corresponding to the constitutively expressed gene for the ribosomal protein L21 (control). FIG. 4b is the expression analysis of p4h1 in moss wild type (WT), the rhEPO producing line 174.16, and five putative moss lines overexpressing p4h1 (No. 12, 16, 32, 41 and 45). Semi-quantitative RT-PCR was performed with increasing cycle number (24, 26 and 28) and primers specific for p4h1 as well as a control with primers corresponding to the constitutively expressed gene encoding the TATA-box binding protein TBP.

Figure 5B:
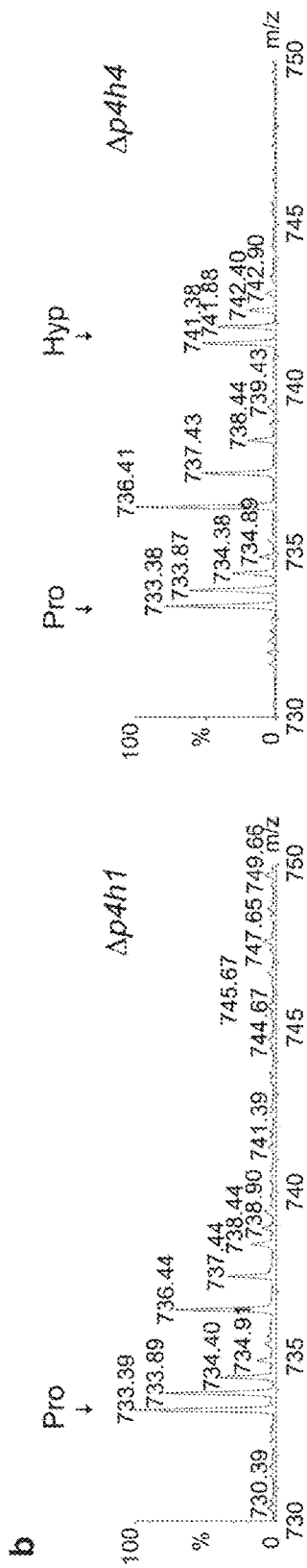
FIG. 5 Mass spectrometric analysis of the hydroxylation of moss-produced rhEPO
Figure 6A:
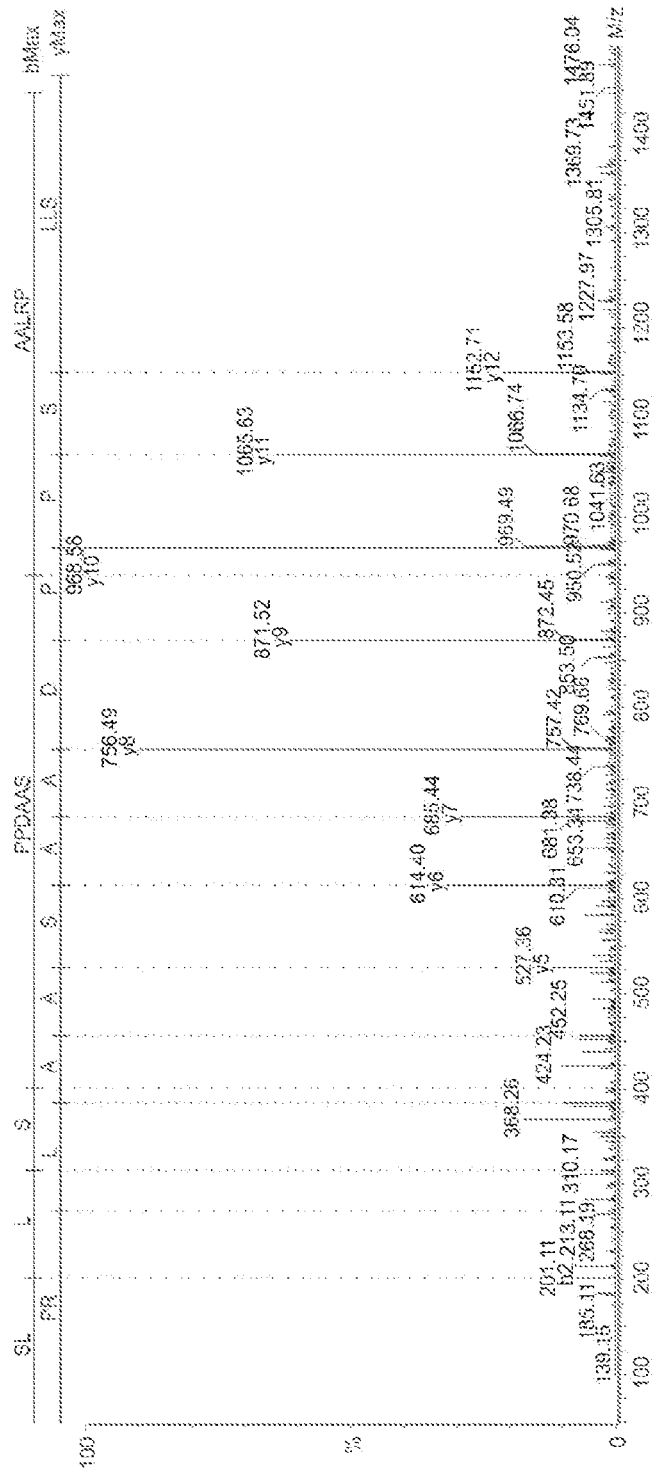
FIG. 6 MS/MS analysis of the peptide EAISPP-DAASAAPLR (144-158) from moss-produced rhEPO FIG. 7 Effect of overexpression of the prolyl-hydroxylase gene p4h1
Figure 6B:
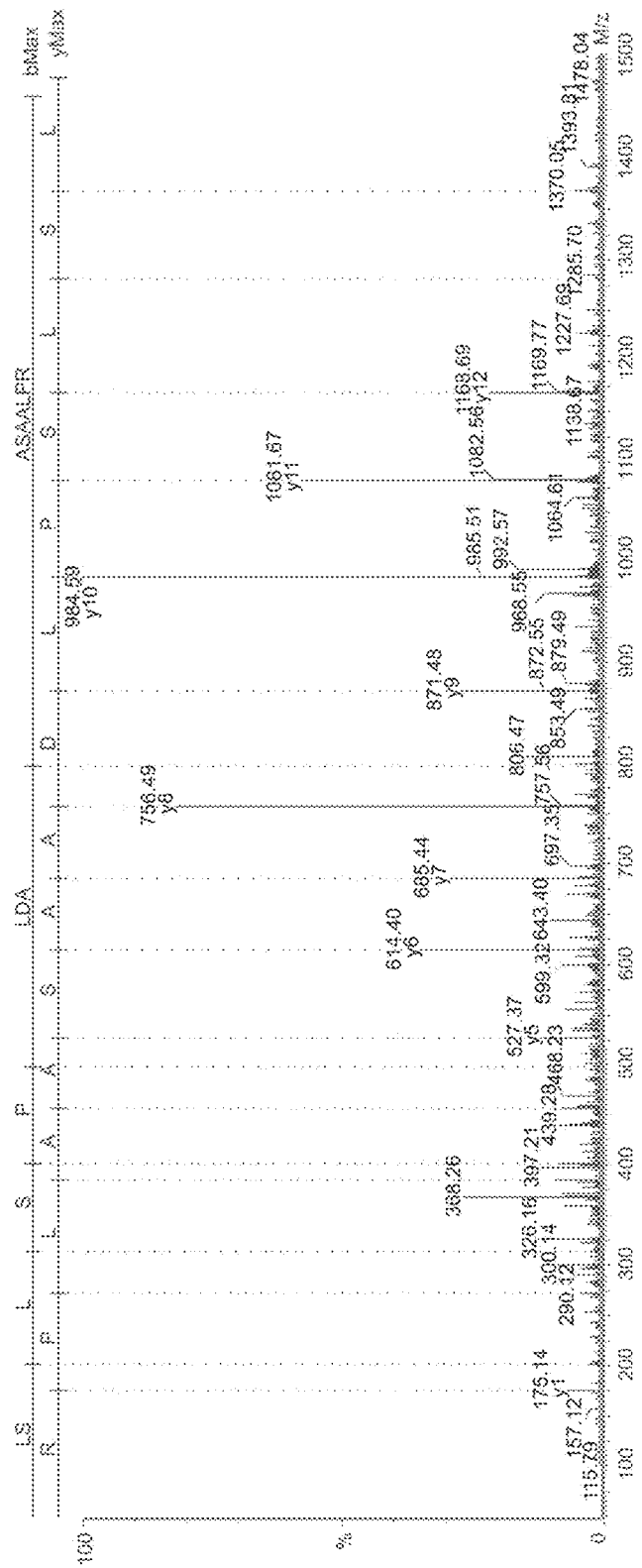

FIGS. 5a and 5b show the mass spectrometric analysis of the hydroxylation of moss-produced rhEPO. FIG. 5a displays the reversed-phase liquid chromatography of tryptic peptides showing peaks of oxidized and non-oxidized peptide EAISPPDAASAAPLR (144-158; SEQ ID NO. 81) derived from rhEPO produced in moss lines 174.16 (control parental plant), Δp4h1 No. 192, Δp4h2 No. 6, Δp4h3 No. 21, Δp4h4 No. 95, Δp4h5 No. 29 and Δp4h6 No. 8. Selected ion chromatograms for the doubly charged ions of non-oxidized (m/z=733.4) and oxidized peptide (m/z 741.4) are shown. FIG. 5b shows broad band sum spectra for peptide 144-158 showing the absence of prolyl-hydroxylation (Pro) in the line Δp4h1 No. 192 and the presence of hydroxylated peptide (Hyp) in the line Δp4h4 No. 95, as an example. The peak between "Pro" and "Hyp" is the incidentally co-eluting peptide YLLEAK (SEQ ID NO. 86). Retention time deviations are technical artifacts FIG. 6 shows the MS/MS analysis of the peptide EAISPPDAASAAPLR (144-158; SEQ ID NO. 81) from moss-produced rhEPO. The one spectrum (FIG. 6a) was derived from non-oxidized peptide (m/z 933.45) faithfully showing the partial sequence SPPDAAS (SEQ ID NO. 83). The other spectrum (FIG. 6b) was derived from one of the two oxidized peptides (m/z 941.45). It gave the apparent partial sequence SPLDAAS (SEQ ID NO. 84), which stands for SPODAAS(SEQ ID NO. 85) as Hyp (0) and Leu isobaric. A second, slightly smaller peak of m/z 941.45 eluted a bit later and probably arose from hydroxylation of the other proline of the hydroxylation motif SPP.

Figure 7A:
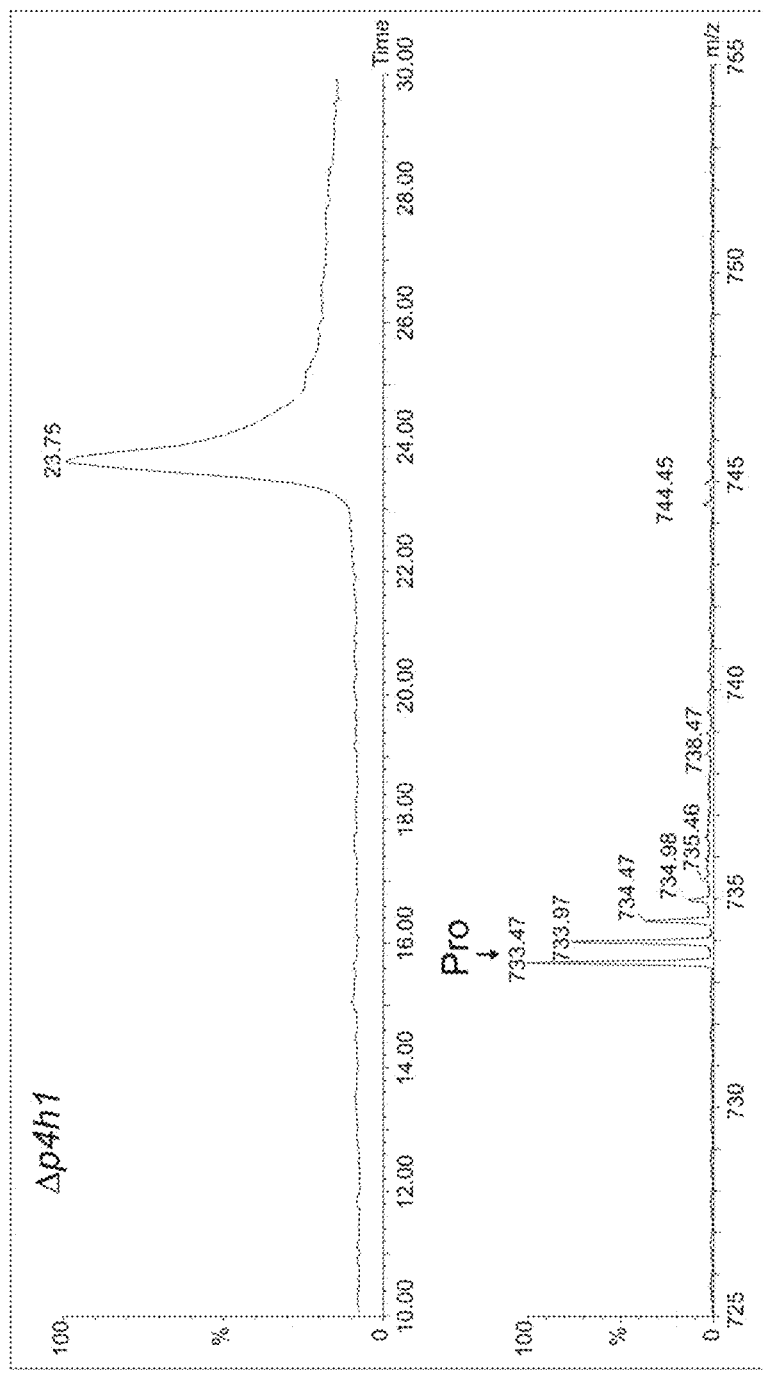
Figure 7B:
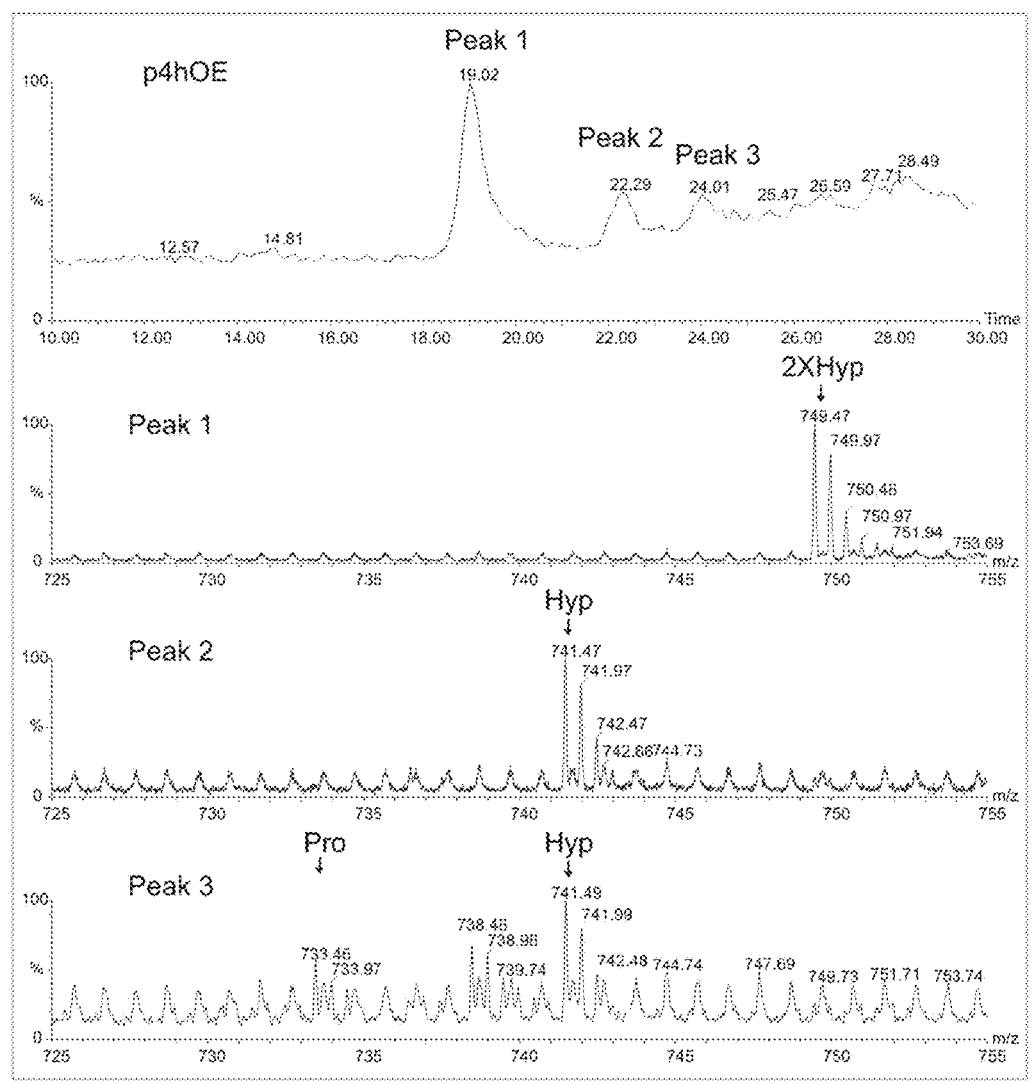

FIG. 7 shows the effect of overexpression of the prolyl-hydroxylase gene p4h1. Comparison of reversed-phase chromatograms showing the retention time for the moss-produced rhEPO peptide EAISPPDAASAAPLR (144-158; SEQ ID NO. 81) and its hydroxylated versions in the knockout moss line Δp4h1 No. 192 (FIG. 7a) and in the overexpressing line p4hOE No. 32 (FIG. 7b). The spectra of each peak are shown below the chromatograms. In the overexpressing line, the doubly hydroxylated peptide and two singly hydroxylated isomers—one coeluting with the parent peptide—were found.

Figure 8:
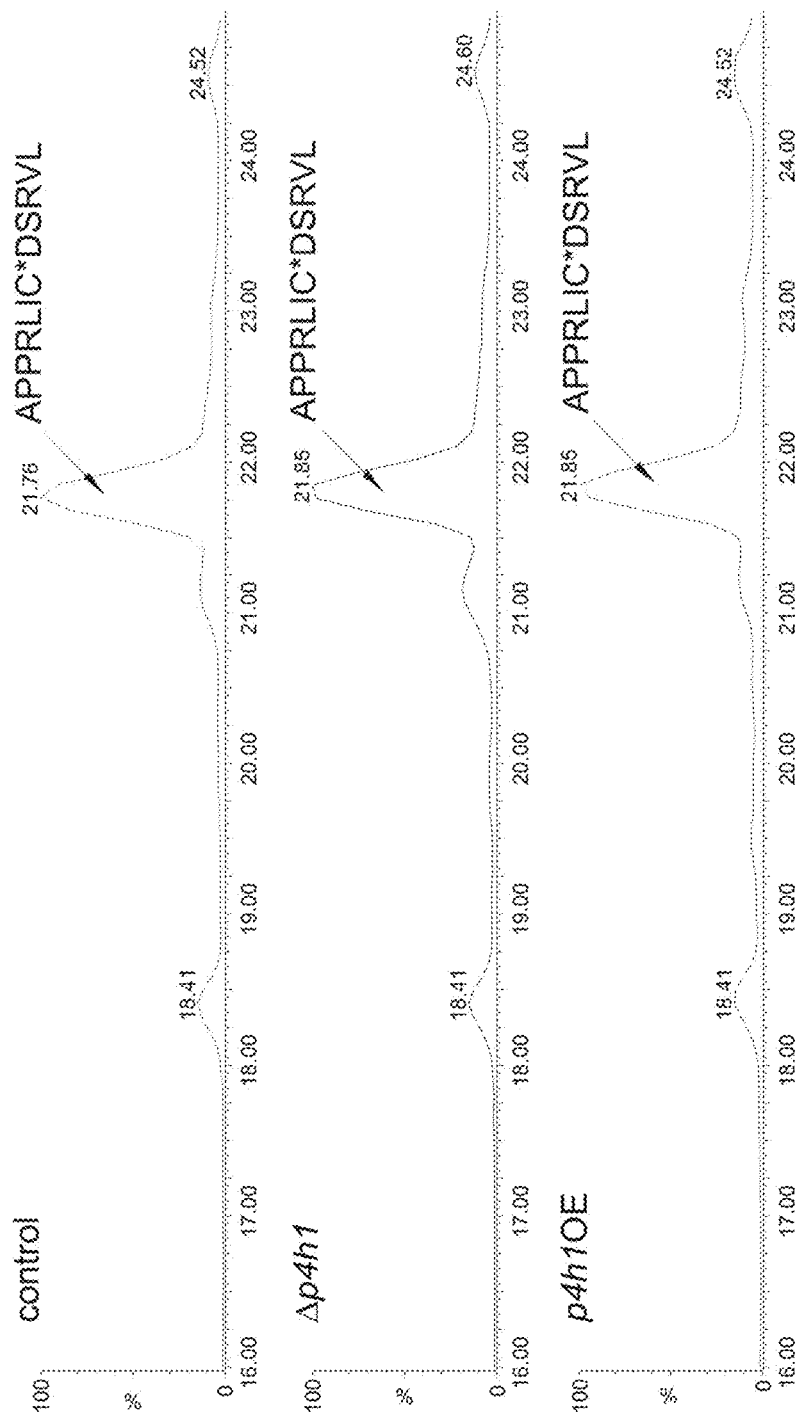
FIG. 8 Analysis of the hydroxylation status of the N-terminal peptide of moss-produced rhEPO FIG. 9 Phylogenetic tree of the amino acid sequences of different plant prolyl-4-hydroxylases

FIG. 8 shows the analysis of the hydroxylation status of the N-terminal peptide of moss-produced rhEPO. The N-terminal sequence APP may also constitute a target sequence for moss prolyl-hydroxylase. Therefore, the N-terminus of moss-produced rhEPO was analyzed by reverse-phase liquid chromatography coupled to electrospray ionization mass spectrometry (LC-ESI-MS) of chymotryptic peptides. Screening for the masses of the non-oxidized and the oxidized peptide APPRLICDSRVL (1-12; SEQ ID NO. 82) from rhEPO produced in moss control line 174.16, the knockout Δp4h1 No. 192 and the overexpression line p4h1OE No. 45 revealed no indication of Pro hydroxylation of this peptide.

Thus, the experiments show the identification and functional characterization of a plant gene responsible for non-human prolyl hydroxylation of recombinant human erythropoietin (rhEPO) produced in moss bioreactors. Targeted ablation of this gene abolished undesired prolyl hydroxylation of rhEPO and thus paves the way for recombinant human proteins produced in a plant-based system humanized via glyco-engineering.

FIG. 9 shows the phylogenetic tree of the amino acid sequences of different plant prolyl-4-hydroxylases. It is shown that the different *Physcomitrella* prolyl-4-hydroxylase genes are not phylogenetically separated from other plants. Rather, the sequence analysis shows that the different prolyl-4-hydroxylases from green algae, mosses and seed plants are very similar to each other and also more similar to each other than within one and the same species. Thus, it is obvious for the person skilled in the art that the disclosed method not only works in *Physcomitrella* but also in other plants.

The present disclosure is not limited to disclosed embodiments as it is obvious for a person skilled in the art that the recombinant human protein may be any protein which is intended to be produced in a plant-based system without adverse prolyl hydroxylation. The disclosed invention is even not restricted to recombinant human proteins and may also be used in the manufacture of proteins from other species, like animals or plants. In addition, other plant-based systems are also possible. It is conceivable that a different prolyl-4-hydroxylase gene is responsible for a different recombinant human protein or a protein from another species and also when using a different plant for the production of the recombinant protein.

SEQUENCE LISTING

<160> NUMBER OF SEQ ID NOS: 86

<210> SEQ ID NO 1
<211> LENGTH: 1352
<212> TYPE: DNA
<213> ORGANISM: Physcomitrella patens

<400> SEQUENCE: 1

```
gcaagatcgt ctgattgcgc gcacgtcgga gatcgcttaa agtgaaggtt gcattgctct      60
ggcaagaagt atttgcaggt aggacggtag agtctggatg cgccagagtt gtcggtttgg     120
ccttcttcgc aagggagaag aagtcatgat gcttggattt agcgaattcg aagagctgat     180
ccttgttttt ccgtcagact ggcaagggat ggagtaattc tacgaagcga gcgcgtcagg     240
gtttggtttt aggaagctgg gctgccacag acacttttga cgatgggtcc ctctagatat     300
gtcattgtgc tcctcacatt tgtgacgatc ggcatggctg gggggcgtt attgcagctg      360 gctttcttga agaagctaga acaaagtagt ggagctggga tttacaatta tagaagagag     420
ataggggaat acgaaaacca aacatttgga tcgggattgt ccctttgggc taatgatgaa     480
gatgcgagaa cactacgtgt tggactggtt aagcaagaag ttattagctg gcaacccaga     540
atcattctcc tgcacaattt ccttagtgct gatgaatgtg atcacctgat aaatcttgct     600
cgccccaggc tcgtgaagtc aacagtcgtg gatgcaacca caggcaaggg aatcgagagt     660
aaggttcgaa caagcacagg catgttcctt aatggaaatg accgcagaca tcacactatt     720
caggcaatcg aaacccgtat tgctgcgtat tctatggtac ctgttcaaaa tggggagctc     780
ctccaagttt tacgatatga atctgatcaa tattacaagg cacatcacga ctactttca      840 gatgagttca atttaaaag gggtgggcaa cgtgtggcga caatgcttat gtacttgacc     900
gagggggtcg agggaggcga aacaatattt ccgcaggctg gagataaaga gtgtagctgt     960
ggcggtgaaa tgaaaatcgg cgtctgtgtg aaacctaaac gagggggatgc tgtcctgttt    1020 tggagcatta agctggatgg acaagttgat ccaacaagcc ttcatggtgg atgcaaagtt    1080
ttgtcaggag agaaatggtc gtctaccaaa tggatgaggc agcgagcctt tgattagggt    1140
gaactttgga tggtaggagc tgtaatcata gtagaagacc aataatagcg attatgcctc    1200
atcattccgg aagctttgcg ggcttttccc gatgcatcta agaatgtatg taatgagcaa    1260
ctttgaatac tgtcagtgat tcgtaacaag aaaaaaaatcg atttagtggt attgtggact    1320
ttgaaatgaa ggttaagatc acgaagagct tt                                  1352
```

<210> SEQ ID NO 2
<211> LENGTH: 284
<212> TYPE: PRT

<213> ORGANISM: Physcomitrella patens

<400> SEQUENCE: 2

```
Met Gly Pro Ser Arg Tyr Val Ile Val Leu Leu Thr Phe Val Thr Ile
1               5                   10                  15

Gly Met Ala Gly Gly Ala Leu Leu Gln Leu Ala Phe Leu Lys Lys Leu
            20                  25                  30

Glu Gln Ser Ser Gly Ala Gly Ile Tyr Asn Tyr Arg Arg Glu Ile Gly
        35                  40                  45

Glu Tyr Glu Asn Gln Thr Phe Gly Ser Gly Leu Ser Leu Trp Ala Asn
    50                  55                  60

Asp Glu Asp Ala Arg Thr Leu Arg Val Gly Leu Val Lys Gln Glu Val
65                  70                  75                  80

Ile Ser Trp Gln Pro Arg Ile Ile Leu Leu His Asn Phe Leu Ser Ala
                85                  90                  95

Asp Glu Cys Asp His Leu Ile Asn Leu Ala Arg Pro Arg Leu Val Lys
            100                 105                 110

Ser Thr Val Val Asp Ala Thr Thr Gly Lys Gly Ile Glu Ser Lys Val
        115                 120                 125

Arg Thr Ser Thr Gly Met Phe Leu Asn Gly Asn Asp Arg Arg His His
    130                 135                 140

Thr Ile Gln Ala Ile Glu Thr Arg Ile Ala Ala Tyr Ser Met Val Pro
145                 150                 155                 160

Val Gln Asn Gly Glu Leu Leu Gln Val Leu Arg Tyr Glu Ser Asp Gln
                165                 170                 175

Tyr Tyr Lys Ala His His Asp Tyr Phe Ser Asp Glu Phe Asn Leu Lys
            180                 185                 190

Arg Gly Gly Gln Arg Val Ala Thr Met Leu Met Tyr Leu Thr Glu Gly
        195                 200                 205

Val Glu Gly Gly Glu Thr Ile Phe Pro Gln Ala Gly Asp Lys Glu Cys
    210                 215                 220

Ser Cys Gly Gly Glu Met Lys Ile Gly Val Cys Val Lys Pro Lys Arg
225                 230                 235                 240

Gly Asp Ala Val Leu Phe Trp Ser Ile Lys Leu Asp Gly Gln Val Asp
                245                 250                 255

Pro Thr Ser Leu His Gly Gly Cys Lys Val Leu Ser Gly Glu Lys Trp
            260                 265                 270

Ser Ser Thr Lys Trp Met Arg Gln Arg Ala Phe Asp
        275                 280
```

<210> SEQ ID NO 3
<211> LENGTH: 1284
<212> TYPE: DNA
<213> ORGANISM: Physcomitrella patens

<400> SEQUENCE: 3

```
gtgatgcgtg atcctgtgct gctgagcgtg ggttttaccg actttaatcg ggcaagggcg      60
ttgatgttaa cttctgcatc gtactggagt gtttgtctac atctccgcgg gaattttctg     120
cgtcttttgg tgtggatcca cagcatggcg ttgagagata gagatgtag tcttattcta      180 gctctcttat tactatcggg attacaagca ttgggagctc gtgtggaaga cttgcctggt     240
tggatggaag aaatcaatga ggtgaaggat gctgagggtg gcgtgattca acaagtttct     300
aggattgatc ccactcgtgt caagcagctt cgtggaaac cgcgtgcatt tctatattca      360 aacttttgt cagatgcaga gtgtgatcat atgatatcgt tggcaaagga caagctggag     420
```

```
aagtcaatgg tggccgataa tgaatctggg aagagtgtga agagtgaaat tcgcactagc    480
tcaggtatgt ttttgatgaa gggtcaggat gatatcatat caaggattga ggataggatt    540
gctgcatgga cctttctacc gaaggagaat ggggaggcaa tccaggtctt gaggtaccaa    600
gatggggaga agtatgagcc acattttgat tatttccacg ataagaacaa tcaggctctt    660
ggaggtcacc gcattgccac tgtgttaatg tacctctccg acgtcgtcaa aggtggagag    720
acagtatttc cttcttctga agatcgaggt ggtcccaagg atgattcgtg gtctgcttgt    780
gggaaaactg gggtggccgt gaaaccaagg aaaggcgatg ccctgctctt cttcagccta    840 caccctctg cagttccaga tgagtcaagc ttacacacag gatgcccagt tatcgaaggg     900
gagaaatggt ctgctacaaa gtggatccat gttgctgcat ttgaaaagcc gcgtcctaag    960
aatggtgcat gtgtaaatga ggtcgacagt tgcgaagagt gggcagctta tggggaatgt   1020
cagaaaaatc cagcctacat ggttgggaca aaagagtggc caggctattg ccggaaagca   1080
tgccatgtgt gctaggtagg gatataccgt atttcttggt tgcactctgt tgggttaggg   1140
taggatattt aatgtatttg tgtcatcatc taagtattag gtcagtttcc aaaccaagga   1200
atcagagttg tggcttttga agaagtatta tagatcttac gtactaatta aaaggcttgt   1260 gaccccttgag atgcactta taat                                          1284

<210> SEQ ID NO 4
<211> LENGTH: 363
<212> TYPE: PRT
<213> ORGANISM: Physcomitrella patens

<400> SEQUENCE: 4

Met Arg Asp Pro Val Leu Leu Ser Val Gly Phe Thr Asp Phe Asn Arg
1               5                   10                  15

Ala Arg Ala Leu Met Leu Thr Ser Ala Ser Tyr Trp Glu Val Cys Leu
            20                  25                  30

His Leu Arg Gly Asn Phe Leu Arg Leu Val Trp Ile His Ser Met
        35                  40                  45

Ala Leu Arg Asp Arg Arg Cys Ser Leu Ile Leu Ala Leu Leu Leu Leu
    50                  55                  60

Ser Gly Leu Gln Ala Leu Gly Ala Arg Val Glu Asp Leu Pro Gly Trp
65                  70                  75                  80

Met Glu Glu Ile Asn Glu Val Lys Asp Ala Gly Gly Val Ile Gln
                85                  90                  95

Gln Val Ser Arg Ile Asp Pro Thr Arg Val Lys Gln Leu Ser Trp Lys
            100                 105                 110

Pro Arg Ala Phe Leu Tyr Ser Asn Phe Leu Ser Asp Ala Glu Cys Asp
        115                 120                 125

His Met Ile Ser Leu Ala Lys Asp Lys Leu Glu Lys Ser Met Val Ala
    130                 135                 140

Asp Asn Glu Ser Gly Lys Ser Val Lys Ser Glu Ile Arg Thr Ser Ser
145                 150                 155                 160

Gly Met Phe Leu Met Lys Gly Gln Asp Ile Ile Ser Arg Ile Glu
                165                 170                 175

Asp Arg Ile Ala Ala Trp Thr Phe Leu Pro Lys Glu Asn Gly Glu Ala
            180                 185                 190

Ile Gln Val Leu Arg Tyr Gln Asp Gly Glu Lys Tyr Glu Pro His Phe
        195                 200                 205

Asp Tyr Phe His Asp Lys Asn Asn Gln Ala Leu Gly Gly His Arg Ile
```

Ala Thr Val Leu Met Tyr Leu Ser Asp Val Val Lys Gly Gly Glu Thr
225                 230                 235                 240

Val Phe Pro Ser Ser Glu Asp Arg Gly Gly Pro Lys Asp Asp Ser Trp
            245                 250                 255

Ser Ala Cys Gly Lys Thr Gly Val Ala Val Lys Pro Arg Lys Gly Asp
        260                 265                 270

Ala Leu Leu Phe Phe Ser Leu His Pro Ser Ala Val Pro Asp Glu Ser
    275                 280                 285

Ser Leu His Thr Gly Cys Pro Val Ile Glu Gly Glu Lys Trp Ser Ala
290                 295                 300

Thr Lys Trp Ile His Val Ala Ala Phe Glu Lys Pro Arg Pro Lys Asn
305                 310                 315                 320

Gly Ala Cys Val Asn Glu Val Asp Ser Cys Glu Trp Ala Ala Tyr
            325                 330                 335

Gly Glu Cys Gln Lys Asn Pro Ala Tyr Met Val Gly Thr Lys Glu Trp
            340                 345                 350

Pro Gly Tyr Cys Arg Lys Ala Cys His Val Cys
        355                 360

<210> SEQ ID NO 5
<211> LENGTH: 1570
<212> TYPE: DNA
<213> ORGANISM: Physcomitrella patens

<400> SEQUENCE: 5
cggcgctttg caactccaat tttgaccagg cgaagtgcac tttgacatct tgttgaatgt      60
cctcttctag agcattgaac ggcccttctg tgaacatttt aaactattca acggatgcca     120
ttgacagtcg tggtttttga agttcgaatc cagagccctc gccatcaaat cgttgcagta     180
atccttggtg atttagcaag ctcgggatca cttcatggat ttggggtcct tcctctgcag     240
aggctgttag tacacacaca ctgcatcaac tcctactggt ctggaagctt ttgaggttgg     300
aaatagtatg aaagagtccc agacaattgg tgtattgagt ggaagagggt tgtgaagttt     360
gggcgctcga ctgaaatgac ctgcgtggat gttagaaaat aagccaattg tgttatgta      420 gagattcgtc acaacgccct cattcctcca acccttaaat gccttgccct atttgtgtac     480
tctcgtgtgc gggaatgacg ctgtccttat acaatatgaa gtcatcgaaa acaaaggaa      540 gaaaatggaa tcctttttaca tacaagctca gtttgccaca ggtgctattg tggtgcacaa    600
tctgcctctt agcaggctat gccgcctcca atttcttccc ccagaaaata gaagaggaag     660
caatatatca gccgtatcgg aaatcggctc agcaagaagg ggaatttcca tttggtgaat     720
tcagtgaaaa agtggtgtta gatcatggta gcactgggga caacttcatc gctgacattc     780 cttttccaggt gttgagctgg aagcctcgtg cgctcttgta tccgagattt gctagcaagg    840
agcaatgcga ggccatcatg aagcttgcaa ggactcgtct tgctccttct gctctggctt    900
tgaggaaagg ggagagtgaa gactcaacga agacatccg aactagttcc gggactttct    960
tgagagccga cgaagacacg acgcggagtt tggagcaagt tgaagagaag atggcgaaag   1020
caaccatgat acctcgcgag aatggagagg ctttcaatgt gttgaagtac aatgtgggac    1080
aaaaatacga ctgccattat gatgtttttg acccagctga gtatggacct caaccaagcc    1140 aacgatggc ctcctttctc ttatatctat cggatgtgga gagggtgga gagaccatgt      1200 ttcccttcga aaattttcaa aacatgaaca taggctttga ctacaagaag tgcattggaa    1260

```
tgaaagtcaa gccccgccaa ggtgatgcat tgcttttcta ctcaatgcat cctaacggca    1320
catttgataa gagcgctctg catggaagct gccctgtaat caaaggcgag aaatgggttg    1380
ccacaaagtg gattcgcaac actgacaaat tttgatcacc accatgcgaa cgttttacg     1440 tccaaaatta ggacatagga atctgtcaat caaattaaag gacatatctt ttatatcatt    1500
taaaaattct gaaactgaga actcatatga acaccagttg aaacattcgg gtcaaccgga    1560
ttatcgacat                                                          1570
```

```
<210> SEQ ID NO 6
<211> LENGTH: 318
<212> TYPE: PRT
<213> ORGANISM: Physcomitrella patens

<400> SEQUENCE: 6

Met Pro Cys Pro Ile Cys Val Leu Ser Cys Ala Gly Met Thr Leu Ser
1               5                   10                  15

Leu Tyr Asn Met Lys Ser Ser Lys Asn Lys Gly Arg Lys Trp Asn Pro
            20                  25                  30

Phe Thr Tyr Lys Leu Ser Leu Pro Gln Val Leu Leu Trp Cys Thr Ile
        35                  40                  45

Cys Leu Leu Ala Gly Tyr Ala Ala Ser Asn Phe Phe Pro Gln Lys Ile
    50                  55                  60

Glu Glu Glu Ala Ile Tyr Gln Pro Tyr Arg Lys Ser Ala Gln Gln Glu
65                  70                  75                  80

Gly Glu Phe Pro Phe Gly Glu Phe Ser Glu Lys Val Val Leu Asp His
                85                  90                  95

Gly Ser Thr Gly Asp Asn Phe Ile Ala Asp Ile Pro Phe Gln Val Leu
            100                 105                 110

Ser Trp Lys Pro Arg Ala Leu Leu Tyr Pro Arg Phe Ala Ser Lys Glu
        115                 120                 125

Gln Cys Glu Ala Ile Met Lys Leu Ala Arg Thr Arg Leu Ala Pro Ser
    130                 135                 140

Ala Leu Ala Leu Arg Lys Gly Glu Ser Glu Asp Ser Thr Lys Asp Ile
145                 150                 155                 160

Arg Thr Ser Ser Gly Thr Phe Leu Arg Ala Asp Glu Asp Thr Thr Arg
                165                 170                 175

Ser Leu Glu Gln Val Glu Glu Lys Met Ala Lys Ala Thr Met Ile Pro
            180                 185                 190

Arg Glu Asn Gly Glu Ala Phe Asn Val Leu Lys Tyr Asn Val Gly Gln
        195                 200                 205

Lys Tyr Asp Cys His Tyr Asp Val Phe Asp Pro Ala Glu Tyr Gly Pro
    210                 215                 220

Gln Pro Ser Gln Arg Met Ala Ser Phe Leu Leu Tyr Leu Ser Asp Val
225                 230                 235                 240

Glu Glu Gly Gly Glu Thr Met Phe Pro Phe Glu Asn Phe Gln Asn Met
                245                 250                 255

Asn Ile Gly Phe Asp Tyr Lys Lys Cys Ile Gly Met Lys Val Lys Pro
            260                 265                 270

Arg Gln Gly Asp Ala Leu Leu Phe Tyr Ser Met His Pro Asn Gly Thr
        275                 280                 285

Phe Asp Lys Ser Ala Leu His Gly Ser Cys Pro Val Ile Lys Gly Glu
    290                 295                 300

Lys Trp Val Ala Thr Lys Trp Ile Arg Asn Thr Asp Lys Phe
305                 310                 315
```

<210> SEQ ID NO 7
<211> LENGTH: 1549
<212> TYPE: DNA
<213> ORGANISM: Physcomitrella patens

<400> SEQUENCE: 7

```
gttacacaaa ttcatcaacc tcgaggcatt tggttcatca gtggatccat ttgttggggt        60
ttcgtgtgga ttgagcttgt gggtttcctt ctccgactcg gaaatcgctc ctgcacagagt      120
tttcacggaa gcttttgagg ctggaaacgg agaaggatta ttccaaagaa tcggttttttt     180
aaagtgtcac ttatcttgtt ttcaaggaca gtctcaataa caatttggcg caattatctg      240
caatgattta catggattga atcgattttc agtagctaaa tgtagggtct gctaggccct      300
ctatattccg acccttgagt gaagacactg cctcccaggc agtccgtgcc ttattttaat      360
ctccttgcgt gcaaagaaca ggaaggctga caccgattat aaacggttga acatgaaaa      420
cgccaaaggt ccgggcaagg agtgcaaacc ctttaagata caagcttggt tttcctctgg      480
tgctcttgtg ttgcacattc ttcttcttgg tcggctttta cggttccaat tccctctcca      540
aggaagaaaa acatgtggtg attgaccccg tcaccaatga aaacttgtg ttcgaacatg       600
gccgtactgg agacagttct gttactgaca ttcctttcca ggtgttaagt tggaaaccac      660
gtgccctttt gtatccgaat tttgcaagca aagagcaatg tgaagccatc atcaagcttg      720
cgaggacacg tcttgctcct tctggtctgg ctttgaggaa aggggagagt gaagccacaa      780
cgaaagaaat cagaactagt tctggaactt tcttgagagc cagtgaagat aaaacacaga      840
gtttagcgga ggttgaggag aagatggcca gagcaaccat gatacctcgg cagaatgggg      900
aggcttttaa tgtgttgcgg tacaacccag gtcaaaaata cgattgtcac tatgatgttt      960
ttgatccagc tgagtatggt cctcaaccaa gccagcggat ggcttccttt ctcctttatt    1020
tatcagacgt cgaagagggc ggagaaacga tgtttcccct cgaaaacttt caaaatatga    1080
acacaggcta taattataag gactgtattg ggttgaaagt gaaaccccgc caaggcgatg    1140
ctcttctttt ctattcaatg catcctaacg gtacatttga caagaccgca ttgcatggaa    1200
gctgtccagt tatcaaaggc gaaaaatggg tcgccacgaa gtggatacgc aataccgaca    1260
aattttaatc tgaaagatcc cactggtgac tgttataact tgctgccttc ttaaagttct    1320
ttcggtagta ctctaggagc ttcaggttat cttacaaaag tatcgggtct gagaaagtgt    1380
aaaatctgtg cgtacctgaa tccatcaatt aagtcatggg tgttatcttt taacattcct    1440
ggtctctgcc aaccagagtt ccagagaaac ggttgttcgc tggattattg ccagcttaaa    1500
gttcacttaa gaaattctaa actcttcaac taagaagaca ttgtccttg                1549
```

<210> SEQ ID NO 8
<211> LENGTH: 284
<212> TYPE: PRT
<213> ORGANISM: Physcomitrella patens

<400> SEQUENCE: 8

Met Lys Thr Pro Lys Val Arg Ala Arg Ser Ala Asn Pro Leu Arg Tyr
1               5                   10                  15

Lys Leu Gly Phe Pro Leu Val Leu Leu Cys Cys Thr Phe Phe Phe Leu
            20                  25                  30

Val Gly Phe Tyr Gly Ser Asn Ser Leu Ser Lys Glu Glu Lys His Val
        35                  40                  45

Val Ile Asp Pro Val Thr Asn Glu Lys Leu Val Phe Glu His Gly Arg

```
                50                    55                    60
Thr Gly Asp Ser Ser Val Thr Asp Ile Pro Phe Gln Val Leu Ser Trp
 65                   70                   75                   80

Lys Pro Arg Ala Leu Leu Tyr Pro Asn Phe Ala Ser Lys Glu Gln Cys
                     85                   90                   95

Glu Ala Ile Ile Lys Leu Ala Arg Thr Arg Leu Ala Pro Ser Gly Leu
                100                  105                  110

Ala Leu Arg Lys Gly Glu Ser Glu Ala Thr Thr Lys Glu Ile Arg Thr
               115                  120                  125

Ser Ser Gly Thr Phe Leu Arg Ala Ser Glu Asp Lys Thr Gln Ser Leu
130                  135                  140

Ala Glu Val Glu Glu Lys Met Ala Arg Ala Thr Met Ile Pro Arg Gln
145                  150                  155                  160

Asn Gly Glu Ala Phe Asn Val Leu Arg Tyr Asn Pro Gly Gln Lys Tyr
                165                  170                  175

Asp Cys His Tyr Asp Val Phe Asp Pro Ala Glu Tyr Gly Pro Gln Pro
                180                  185                  190

Ser Gln Arg Met Ala Ser Phe Leu Leu Tyr Leu Ser Asp Val Glu Glu
               195                  200                  205

Gly Gly Glu Thr Met Phe Pro Phe Glu Asn Phe Gln Asn Met Asn Thr
210                  215                  220

Gly Tyr Asn Tyr Lys Asp Cys Ile Gly Leu Lys Val Lys Pro Arg Gln
225                  230                  235                  240

Gly Asp Ala Leu Leu Phe Tyr Ser Met His Pro Asn Gly Thr Phe Asp
                245                  250                  255

Lys Thr Ala Leu His Gly Ser Cys Pro Val Ile Lys Gly Glu Lys Trp
                260                  265                  270

Val Ala Thr Lys Trp Ile Arg Asn Thr Asp Lys Phe
               275                  280

<210> SEQ ID NO 9
<211> LENGTH: 1689
<212> TYPE: DNA
<213> ORGANISM: Physcomitrella patens

<400> SEQUENCE: 9
gctgcttcag ggtaggacaa accatcgtcg aaggggatgt gggtcgacct attttggtca      60
actttatctg tctttctact tccgatgaat tgccgttttt gttgtaagcg tttgcacatg     120
caggttggag gctggtgaac tgcatacaca aatttgatag tcggggagaa agaggagttt     180
ctcacagtgt ctttggtgat tggatcatcc tcgaggagct tttagctcga agggtttcct     240
gattttaagt ttggaaccga ggtatttcaa tcgtgagagt ggttcttagc atgcatacat     300
tttgagtgtg taggtatgga tctctattct agaagccgta gaggctgagt aactattgca     360
ttctctgaaa tcctgtttac ctcggcgcgg ccacatctcg aagtagtcgg taattttctt     420
ccttgggttt cgtgggagcc gggcgaagtt cgtaactatg cgaagctga gtcgaggtca      480 aaggagagga gctggcacga tggctttgtt ggtgctggtc ctgttgtctc tagcgctcat     540
gctcatgttg gcacttggct ttgtagccat gccatcggcg tcccacggga gttcggctga     600
cgttgtggaa atcaagctgc cctcacacag gcattttggt gccaacccct tatcacgttg     660
ggttgaagtc ctctcttggg agcccagagc ctttctatat caccactttc tgacagaaga     720
ggaatgcaat catctaattg aagtggccag gccaagtctg gtgaagtcaa cggttgtaga     780
tagtgataca ggaaagagca agacagcag agtacgcaca agttcaggta cattttgat      840
```

```
gcgaggccaa gatcctgtga tcaaaagaat cgagaagcga atagctgact tcacatttat    900
acctgctgag caaggtgaag gcttacaagt tctgcagtac aaagaaagtg aaaaatacga    960
gccccattat gattacttcc acgatgcata caataccaaa aatggcggcc aaagaattgc   1020
taccgtactg atgtacctgt caatgtcga ggaaggagga gaaacagttt ttccagctgc   1080
tcaggtgaac aagactgaag ttcccgattg ggataaatta tctgagtgtg ctcagaaagg   1140
tctttctgtg cgaccacgca tgggagatgc cttgcttttc tggagcatga aaccagatgc   1200
gacacttgat tccactagct tgcatggtgg ctgccccgtg atcaagggta ccaaatggtc   1260
tgctactaag tggttacatg tagaaaacta tgcagcctga tgaggatggt acaagatgtc   1320
ttctgcagga agtgaattgt cacaagcacc tggtacaagc agattcgaaa tgcttggatg   1380
taatgcatgg atgttgggag aggacaaaca tacaaattta tgattctgca ttacgtgaga   1440
tgtaatgatg aaccacctcg tgcctatctg aattcatatg aacaaacgaa tagatttcca   1500
attcatacca ataaaacaga aaagccgctt aacttatttg ttaacttagg cagttttttt   1560
gttttattat tggtggtttg caatcgacct taacgaccat ttcttgtaat caccacaaac   1620
aagcaaaatg catatctgat ttcattcaaa atatacttat aaagactgct gaatctataa   1680
caaacaaaa                                                           1689

<210> SEQ ID NO 10
<211> LENGTH: 280
<212> TYPE: PRT
<213> ORGANISM: Physcomitrella patens

<400> SEQUENCE: 10

Met Ala Lys Leu Ser Arg Gly Gln Arg Arg Gly Ala Gly Thr Met Ala
1               5                   10                  15

Leu Leu Val Leu Val Leu Leu Ser Leu Ala Leu Met Leu Met Leu Ala
                20                  25                  30

Leu Gly Phe Val Ala Met Pro Ser Ala Ser His Gly Ser Ser Ala Asp
            35                  40                  45

Val Val Glu Ile Lys Leu Pro Ser His Arg His Phe Gly Ala Asn Pro
        50                  55                  60

Leu Ser Arg Trp Val Glu Val Leu Ser Trp Glu Pro Arg Ala Phe Leu
65                  70                  75                  80

Tyr His His Phe Leu Thr Glu Glu Glu Cys Asn His Leu Ile Glu Val
                85                  90                  95

Ala Arg Pro Ser Leu Val Lys Ser Thr Val Val Asp Ser Asp Thr Gly
            100                 105                 110

Lys Ser Lys Asp Ser Arg Val Arg Thr Ser Ser Gly Thr Phe Leu Met
        115                 120                 125

Arg Gly Gln Asp Pro Val Ile Lys Arg Ile Glu Lys Arg Ile Ala Asp
    130                 135                 140

Phe Thr Phe Ile Pro Ala Glu Gln Gly Glu Gly Leu Gln Val Leu Gln
145                 150                 155                 160

Tyr Lys Glu Ser Glu Lys Tyr Glu Pro His Tyr Asp Tyr Phe His Asp
                165                 170                 175

Ala Tyr Asn Thr Lys Asn Gly Gly Gln Arg Ile Ala Thr Val Leu Met
            180                 185                 190

Tyr Leu Ser Asn Val Glu Glu Gly Gly Glu Thr Val Phe Pro Ala Ala
        195                 200                 205

Gln Val Asn Lys Thr Glu Val Pro Asp Trp Asp Lys Leu Ser Glu Cys
```

```
        210                 215                 220
Ala Gln Lys Gly Leu Ser Val Arg Pro Arg Met Gly Asp Ala Leu Leu
225                 230                 235                 240

Phe Trp Ser Met Lys Pro Asp Ala Thr Leu Asp Ser Thr Ser Leu His
            245                 250                 255

Gly Gly Cys Pro Val Ile Lys Gly Thr Lys Trp Ser Ala Thr Lys Trp
        260                 265                 270

Leu His Val Glu Asn Tyr Ala Ala
        275                 280

<210> SEQ ID NO 11
<211> LENGTH: 1565
<212> TYPE: DNA
<213> ORGANISM: Physcomitrella patens

<400> SEQUENCE: 11
gaaaaagagc agcagttgga gttggagtag gccagatcga tgctcctcct cctcccatga    60
tgatagatga cgaagattat gctgttgttg tcgatgttgt tgctcgctga tcatcaacac   120
gaagttgccg ttgcagctgc tcttgctctt caccgtcgac tcggcagagg ggcacagctc   180
agctggtaat ttattattag tgcccatggg tgggatggat gtgagtgaca tcggcgcttc   240
taccgacagt gtgaaacccc agcgaggctg tgccttgcct tgccttggct tgtgtgcatt   300
gcctctcccc tccagttttt tggtgggttg gtgtttgtgt gagggggggaa cagaggagag   360 ggcgggggca agggctgtgg cagctatggc gaggttgagt aggggggcaaa ggactggagt   420 tggcacgatg gcattgctgg tgttcgcgtt tttgtctttg atagtcatgg tcatgttgct   480
tctggacgtg gtagcaatgc catcgggacg tcgaggctcg attgacgagg agccgaagt    540 ggaattgaag ctgcctaccc acaggcatgt ggatgaaaat ccactggcac cttgggttga   600
ggtcctttcc tgggagccca gcttttctc gtatcaccac tttctgacac aagtggaatg   660
caaccatctt attgaggtgg ccaagcctag cctggtgaag tcaacagtta tagatagtgc   720
tacgggaaaa agcaaagaca gcagggttcg cacaagttca gggacatttt tggtgcgggg   780
ccaagatcac atcattaaga ggattgagaa acgtatcgct gacttcacat tcatacctgt   840
tgaacaaggt gaaggcttgc aagttttgca gtatagagag agtgagaaat acgagcctca   900
ttatgactac tttcacgatg ctttcaatac taaaaatggt ggtcagcgga ttgctaccgt   960
actgatgtat ctgtcagacg ttgagaaagg gggagaaaca gttttcccgg cttctaaagt  1020
gaacgctagt gaggttcctg attgggatca gcgatccgaa tgcgctaaac ggggcctttc  1080
tgtacgacca cgtatgggag atgccttact tttttggagc atgaaaccag atgcgaagct  1140 tgacctacc agtttgcatg gcgcttgccc tgtgattcaa ggtacgaaat ggtctgctac  1200
aaagtggtta catgttgaaa aatacgcagc acggtaaaca tccttctaga agtcttcaac  1260
aggattacat gaattatgcg agcagtcttc tggcatgagc agaggtgaac ttgcccaaac  1320
ttgctcatgg aacaacagaa tcagcttgcg agttatttac aaggagcgag tgtccatgcc  1380
tgaatgctgg aacaccagcg tgatgagaac gcttaggaat accaattctt cactgatttt  1440
acaaaccaca ctagctacta cacatgacaa atttcatgct ttgacttggt tgatctgctt  1500
ttgtgtgagg atcagtattt tataaatagg ggatggagct cttcagctcc taatgtgcga  1560
tttcg                                                               1565

<210> SEQ ID NO 12
<211> LENGTH: 343
```

```
<212> TYPE: PRT
<213> ORGANISM: Physcomitrella patens

<400> SEQUENCE: 12

Met Gly Gly Met Asp Val Ser Asp Ile Gly Ala Ser Thr Asp Ser Val
1               5                   10                  15

Lys Pro Gln Arg Gly Cys Ala Leu Pro Cys Leu Gly Leu Cys Ala Leu
            20                  25                  30

Pro Leu Pro Ser Ser Phe Leu Val Gly Trp Cys Leu Cys Glu Gly Gly
        35                  40                  45

Thr Glu Glu Arg Ala Gly Ala Arg Ala Val Ala Ala Met Ala Arg Leu
    50                  55                  60

Ser Arg Gly Gln Arg Thr Gly Val Gly Thr Met Ala Leu Leu Val Phe
65                  70                  75                  80

Ala Phe Leu Ser Leu Ile Val Met Val Met Leu Leu Leu Asp Val Val
                85                  90                  95

Ala Met Pro Ser Gly Arg Arg Gly Ser Ile Asp Glu Gly Ala Glu Val
            100                 105                 110

Glu Leu Lys Leu Pro Thr His Arg His Val Asp Glu Asn Pro Leu Ala
        115                 120                 125

Pro Trp Val Glu Val Leu Ser Trp Glu Pro Arg Ala Phe Leu Tyr His
    130                 135                 140

His Phe Leu Thr Gln Val Glu Cys Asn His Leu Ile Glu Val Ala Lys
145                 150                 155                 160

Pro Ser Leu Val Lys Ser Thr Val Ile Asp Ser Ala Thr Gly Lys Ser
                165                 170                 175

Lys Asp Ser Arg Val Arg Thr Ser Gly Thr Phe Leu Val Arg Gly
            180                 185                 190

Gln Asp His Ile Ile Lys Arg Ile Glu Lys Arg Ile Ala Asp Phe Thr
        195                 200                 205

Phe Ile Pro Val Glu Gln Gly Glu Gly Leu Gln Val Leu Gln Tyr Arg
    210                 215                 220

Glu Ser Glu Lys Tyr Glu Pro His Tyr Asp Tyr Phe His Asp Ala Phe
225                 230                 235                 240

Asn Thr Lys Asn Gly Gly Gln Arg Ile Ala Thr Val Leu Met Tyr Leu
                245                 250                 255

Ser Asp Val Glu Lys Gly Gly Thr Val Phe Pro Ala Ser Lys Val
            260                 265                 270

Asn Ala Ser Glu Val Pro Asp Trp Asp Gln Arg Ser Glu Cys Ala Lys
        275                 280                 285

Arg Gly Leu Ser Val Arg Pro Arg Met Gly Asp Ala Leu Leu Phe Trp
    290                 295                 300

Ser Met Lys Pro Asp Ala Lys Leu Asp Pro Thr Ser Leu His Gly Ala
305                 310                 315                 320

Cys Pro Val Ile Gln Gly Thr Lys Trp Ser Ala Thr Lys Trp Leu His
                325                 330                 335

Val Glu Lys Tyr Ala Ala Arg
            340

<210> SEQ ID NO 13
<211> LENGTH: 1602
<212> TYPE: DNA
<213> ORGANISM: Physcomitrella patens

<400> SEQUENCE: 13
```

-continued

| | |
|---|---|
| gaaaaagagc agcagttgga gttggagtag gccagatcga tgctcctcct cctcccatga | 60 |
| tgatagatga cgaagattat gctgttgttg tcgatgttgt tgctcgctga tcatcaacac | 120 |
| gaagttgccg ttgcagctgc tcttgctctt caccgtcgac tcggcagagg ggcacagctc | 180 |
| agctggtaat ttattattag tgcccatggg tgggatggga gtgagtgaca tcggcgcttc | 240 |
| taccgacagt gtgaaacccc agcgaggctg tgccttgcct tgccttggct tgtgtgcatt | 300 |
| gcctctcccc tccagtcgta attgagacgt actattaaac acgtaggcgg tagttttttgg | 360 |
| tgggttggtg tttgtgtgag gggggaacag aggagagggc gggggcaagg gctgtggcag | 420 |
| ctatggcgag gttgagtagg gggcaaagga ctggagttgg cacgatggca ttgctggtgt | 480 |
| tcgcgttttt gtctttgata gtcatggtca tgttgcttct ggacgtggta gcaatgccat | 540 |
| cgggacgtcg aggctcgatt gacgaggggag ccgaagtgga attgaagctg cctacccaca | 600 |
| ggcatgtgga tgaaaatcca ctggcacctt gggttgaggt cctttcctgg agcccagag | 660 |
| cttttctgta tcaccacttt ctgacacaag tggaatgcaa ccatcttatt gaggtggcca | 720 |
| agcctagcct ggtgaagtca acagttatag atagtgctac gggaaaaagc aaagacagca | 780 |
| gggttcgcac aagttcaggg acattttttgg tgcggggcca agatcacatc attaaggaga | 840 |
| ttgagaaacg tatcgctgac ttcacattca tacctgttga acaaggtgaa ggcttgcaag | 900 |
| ttttgcagta tagagagagt gagaaatacg agcctcatta tgactacttt cacgatgctt | 960 |
| tcaatactaa aaatggtggt cagcggattg ctaccgtact gatgtatctg tcagacgttg | 1020 |
| agaaaggggg agaaacagtt tccccggctt ctaaagtgaa cgctagtgag gttcctgatt | 1080 |
| gggatcagcg atccgaatgc gctaaacggg gcctttctgt acgaccacgt atgggagatg | 1140 |
| ccttactttt ttggagcatg aaaccagatg cgaagcttga ccctaccagt ttgcatggcg | 1200 |
| cttgccctgt gattcaaggt acgaaatggt ctgctacaaa gtggttacat gttgaaaaat | 1260 |
| acgcagcacg gtaaacatcc ttctagaagt cttcaacagg attacatgaa ttatgcgagc | 1320 |
| agtcttctgg catgagcaga ggtgaacttg cccaaacttg ctcatggaac aacagaatca | 1380 |
| gcttgcgagt tatttacaag gagcgagtgt ccatgcctga atgctggaac accagcgtga | 1440 |
| tgagaacgct taggaatacc aattcttcac tgattttaca aaccacacta gctactacac | 1500 |
| atgacaaatt tcatgctttg acttggttga tctgcttttg tgtgaggatc agtattttat | 1560 |
| aaataggga tggagctctt cagctcctaa tgtgcgattt cg | 1602 |

<210> SEQ ID NO 14
<211> LENGTH: 283
<212> TYPE: PRT
<213> ORGANISM: Physcomitrella patens

<400> SEQUENCE: 14

Met Ala Arg Leu Ser Arg Gly Gln Arg Thr Gly Val Gly Thr Met Ala
1               5                   10                  15

Leu Leu Val Phe Ala Phe Leu Ser Leu Ile Val Met Val Met Leu Leu
            20                  25                  30

Leu Asp Val Val Ala Met Pro Ser Gly Arg Arg Gly Ser Ile Asp Glu
        35                  40                  45

Gly Ala Glu Val Glu Leu Lys Leu Pro Thr His Arg His Val Asp Glu
    50                  55                  60

Asn Pro Leu Ala Pro Trp Val Glu Val Leu Ser Trp Glu Pro Arg Ala
65                  70                  75                  80

Phe Leu Tyr His His Phe Leu Thr Gln Val Glu Cys Asn His Leu Ile
                85                  90                  95

```
Glu Val Ala Lys Pro Ser Leu Val Lys Ser Thr Val Ile Asp Ser Ala
            100                 105                 110
Thr Gly Lys Ser Lys Asp Ser Arg Val Arg Thr Ser Ser Gly Thr Phe
        115                 120                 125
Leu Val Arg Gly Gln Asp His Ile Ile Lys Arg Ile Glu Lys Arg Ile
    130                 135                 140
Ala Asp Phe Thr Phe Ile Pro Val Glu Gln Gly Glu Gly Leu Gln Val
145                 150                 155                 160
Leu Gln Tyr Arg Glu Ser Glu Lys Tyr Glu Pro His Tyr Asp Tyr Phe
                165                 170                 175
His Asp Ala Phe Asn Thr Lys Asn Gly Gly Gln Arg Ile Ala Thr Val
            180                 185                 190
Leu Met Tyr Leu Ser Asp Val Glu Lys Gly Gly Glu Thr Val Phe Pro
        195                 200                 205
Ala Ser Lys Val Asn Ala Ser Glu Val Pro Asp Trp Asp Gln Arg Ser
    210                 215                 220
Glu Cys Ala Lys Arg Gly Leu Ser Val Arg Pro Arg Met Gly Asp Ala
225                 230                 235                 240
Leu Leu Phe Trp Ser Met Lys Pro Asp Ala Lys Leu Asp Pro Thr Ser
                245                 250                 255
Leu His Gly Ala Cys Pro Val Ile Gln Gly Thr Lys Trp Ser Ala Thr
            260                 265                 270
Lys Trp Leu His Val Glu Lys Tyr Ala Ala Arg
        275                 280

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gggatggagt aattctacga agc                                            23

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aatcaaaggc tcgctgcctc at                                             22

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gtgatgcgtg atcctgtgc                                                 19

<210> SEQ ID NO 18
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ggcacacatg gcatgctttc                                                     20

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ggtgttatgt agagattcgt cacaac                                              26

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gaaatttgtc agtgttgcga atc                                                 23

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gactcggaaa tcgctcctga                                                     20

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gaaatttgtc ggtattgcgt atc                                                 23

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gccacatctc gaagtagtcg gtaat                                               25

<210> SEQ ID NO 24
<211> LENGTH: 26
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 24
cggctgcata gttttctaca tgtaac                                              26

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ctcttgctct tcaccgtcga ctc                                                 23

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
accgtgctgc gtattttca ac                                                   22

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gagacgtact attaaacacg tagg                                                24

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
accgtgctgc gtattttca ac                                                   22

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tgaattctga atgtcataag gcctctactg                                          30

<210> SEQ ID NO 30
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 30
tgaattcaga gggtaggatt gtgtgaag                                       28

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cgaattcctc tgctccctgt tcttgtttg                                      29

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cgaattccac aaacttcatc gacttgatcc                                     30

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gaattcgttg cagtaatcct tggtgat                                        27

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gaattctctc caccctcttc cacatc                                         26

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tgaattcctg aggggattga agag                                           24

<210> SEQ ID NO 36
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 36
tgaattcaga acacagggat cagc                                          24

<210> SEQ ID NO 37
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tgaattctgc agcttgttac actcccaat                                     29

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
atgaattcag ataggcacga ggtggt                                        26

<210> SEQ ID NO 39
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tgaattctgc agtagatggc caatcatgt                                     29

<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gtaatcctgc aacaagaatt caaagcag                                      28

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ggctaatgat gaagatgcga ga                                            22

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 42
tgtcgtgctc caccatgttg                                          20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gttgagcata taagaaaccc                                          20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
agcatcccct cgtttaggtt                                          20

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tgtggtattc tcgcagatta ggg                                      23

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
tgtcgtgctc caccatgttg                                          20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gttgagcata taagaaaccc                                          20

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
cggtcataat ttgagttttg ct                                          22

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
caacggatgc cattgacagt                                             20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tgtcgtgctc caccatgttg                                             20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gttgagcata taagaaaccc                                             20

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
catttggcaa cttaagggtg ta                                          22

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gactcggaaa tcgctcctga                                             20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 54
tgtcgtgctc caccatgttg                                                    20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gttgagcata taagaaaccc                                                    20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
catcgacagt tgttcgtgga                                                    20

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gtaaaggaca ttcgtttatg catcg                                              25

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
tgtcgtgctc caccatgttg                                                    20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gttgagcata taagaaaccc                                                    20

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
```
tgtggtgatt acaagaaatg gtcgt                                        25

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ataggtgtcg ctacagcaat cg                                           22

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
tgtcgtgctc caccatgttg                                              20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gttgagcata taagaaaccc                                              20

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
atggacactc gctccttgta a                                            21

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gggatggagt aattctacga ag                                           22

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ctaatcaaag gctcgctgcc tcat                                              24

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ggctaatgat gaagatgcga ga                                                22

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
agcatcccct cgtttaggtt                                                   20

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
aggacaagct ggagaagtca atg                                               23

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gcctagcaca catggcatg                                                    19

<210> SEQ ID NO 71
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
ggtgttatgt agagattcgt cacaac                                            26

<210> SEQ ID NO 72
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
gaattctctc caccctcttc cacatc                                            26

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ttggtcggct tttacggttc                                              20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
aaagaagagc atcgccttgg                                              20

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
tcctgttgtc tctagcgctc at                                           22

<210> SEQ ID NO 76
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
cggctgcata gttttctaca tgtaac                                       26

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ccagagcttt tctgtatcac cac                                          23

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
accgtgctgc gtattttca ac                                            22

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gctgaggcag tcttggag                                                 18

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tcgagccgga tagggaac                                                 18

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Tryptic fragment of rhEPO

<400> SEQUENCE: 81

Glu Ala Ile Ser Pro Pro Asp Ala Ala Ser Ala Ala Pro Leu Arg
1               5                   10                  15

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-terminal fragment rhEPO

<400> SEQUENCE: 82

Ala Pro Pro Arg Leu Ile Cys Asp Ser Arg Val Leu
1               5                   10

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Partial sequence tryptic fragment rhEPO

<400> SEQUENCE: 83

Ser Pro Pro Asp Ala Ala Ser
1               5

<210> SEQ ID NO 84
<211> LENGTH: 7
<212> TYPE: PRT
<213> ORGANISM: Artificial Sequence -continued

```
<220> FEATURE:
<223> OTHER INFORMATION: Description of Artificial Sequence: Synthetic
      peptide
<220> FEATURE:
<223> OTHER INFORMATION: Partial sequence tryptic fragment rhEPO

<400> SEQUENCE: 84

Ser Pro Leu Asp Ala Ala Ser
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Partial sequence tryptic fragment rhEPO
<220> FEATURE:
<221> NAME/KEY: MOD_RES
<222> LOCATION: (3)..(3)
<223> OTHER INFORMATION: Hydroxy proline

<400> SEQUENCE: 85

Ser Pro Pro Asp Ala Ala Ser
1               5

<210> SEQ ID NO 86
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Co-eluting peptide rhEPO

<400> SEQUENCE: 86

Tyr Leu Leu Glu Ala Lys
1               5
```

The invention claimed is:

1. Cells derived from *Physcomitrella patens*, comprising an ablation of expression of the plant endogenous prolyl-4-hydroxylase 1 gene according to SEQ ID NO: 1 or comprising a down-regulation of expression of the plant endogenous prolyl-4-hydroxylase 1 gene according to SEQ ID NO: 1 by amiRNA or antisense RNA.

2. Plant cells derived from *Physcomitrella patens*, according to claim 1, wherein the ablation of expression of the plant endogenous prolyl-4-hydroxylase 1 gene comprises knockout of the prolyl-4-hydroxylase 1 gene.

3. A method for the manufacture of a recombinant protein comprising the steps of:
   providing cells according to claim 1;
   delivering a gene encoding the recombinant protein into said cells; and
   cultivating said cells for the expression of the gene encoding the recombinant protein.

4. The method according to claim 3 for the manufacture of recombinant human erythropoietin (rhEPO).

* * * * *